United States Patent
Levine et al.

(10) Patent No.: US 8,639,525 B2
(45) Date of Patent: Jan. 28, 2014

(54) DRUG LABELING

(75) Inventors: Wilton C. Levine, Needham, MA (US); James Kenneth Davison, Needham, MA (US); Michael Dempsey, Groton, MA (US); Kimberly Donovan, Milton, MA (US); William D. Driscoll, III, Salem, MA (US); Gayle A. Fishman, Wellesley Hills, MA (US); Nathaniel M. Sims, Milton, MA (US)

(73) Assignee: Codonics, Inc., Middleburg Heights, OH (US)

( * ) Notice: Subject to any disclaimer, the term of this patent is extended or adjusted under 35 U.S.C. 154(b) by 588 days.

(21) Appl. No.: 12/581,047

(22) Filed: Oct. 16, 2009

(65) Prior Publication Data

US 2011/0093279 A1    Apr. 21, 2011

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC .................... 705/2–3, 28; 235/375, 385, 562; 604/189
See application file for complete search history.

(56) References Cited

U.S. PATENT DOCUMENTS

| | | | |
|---|---|---|---|
| 4,652,317 A | 3/1987 | Seestrom |
| 4,835,372 A | 5/1989 | Gombrich et al. |
| 4,853,521 A | 8/1989 | Claeys et al. |
| 4,857,713 A | 8/1989 | Brown |
| 4,921,277 A | 5/1990 | McDonough |
| 4,925,444 A | 5/1990 | Orkin et al. |
| 4,978,335 A | 12/1990 | Arthur, III |
| 5,048,870 A | 9/1991 | Mangini et al. |
| 5,078,683 A | 1/1992 | Sancoff et al. |
| 5,207,642 A | 5/1993 | Orkin et al. |
| 5,317,506 A | 5/1994 | Coutre et al. |
| 5,378,231 A | 1/1995 | Johnson et al. |
| 5,381,487 A | 1/1995 | Shamos |

(Continued)

FOREIGN PATENT DOCUMENTS

| | | |
|---|---|---|
| CA | 2534596 | 7/2007 |
| WO | 2008/019494 | 2/2008 |
| WO | 2009/049133 | 4/2009 |

OTHER PUBLICATIONS

International Search Report and Written Opinion in PCT/US2010/050007, mailed Apr. 29, 2011, 9 pages.

(Continued)

*Primary Examiner* — Michelle L Le
(74) *Attorney, Agent, or Firm* — Pearne & Gordon LLP

(57) ABSTRACT

Disclosed are systems and methods for enabling transfer of a drug from a first drug container to a second drug container including a drug identification component that recognizes a first drug container to retrieve drug identifying data for the drug, a storage medium that stores a site-specific database comprising attributes and associated values for a set of drugs including the drug in the first drug container, a processor that obtains the drug identifying data and the attributes and associated values for the drug and produces information about the drug using the drug identifying data and the attributes and associated values, a rules engine that applies one or more rules to the information about the drug to generate drug handling information, and an output unit that outputs markings comprising the drug handling information in human-readable or machine-readable form, or both, to be associated with the second container.

38 Claims, 13 Drawing Sheets

(56) References Cited

U.S. PATENT DOCUMENTS

| | | | |
|---|---|---|---|
| 5,401,110 A | 3/1995 | Neeley | |
| 5,508,499 A | 4/1996 | Ferrario | |
| 5,592,374 A | 1/1997 | Fellegara et al. | |
| 5,651,775 A | 7/1997 | Walker et al. | |
| 5,681,285 A | 10/1997 | Ford et al. | |
| 5,692,640 A | 12/1997 | Caulfield et al. | |
| 5,700,998 A | 12/1997 | Palti | |
| 5,713,856 A | 2/1998 | Eggers et al. | |
| 5,800,387 A | 9/1998 | Duffy et al. | |
| 5,845,264 A | 12/1998 | Nellhaus | |
| 5,855,395 A | 1/1999 | Foote et al. | |
| 5,883,370 A | 3/1999 | Walker et al. | |
| 6,021,392 A | 2/2000 | Lester et al. | |
| 6,036,231 A | 3/2000 | Foote et al. | |
| 6,098,892 A | 8/2000 | Peoples, Jr. | |
| D438,634 S | 3/2001 | Merry | |
| 6,260,761 B1 | 7/2001 | Peoples, Jr. | |
| 6,269,340 B1 | 7/2001 | Ford et al. | |
| 6,317,719 B1* | 11/2001 | Schrier et al. | 705/2 |
| 6,339,732 B1 | 1/2002 | Phoon et al. | |
| 6,542,902 B2 | 4/2003 | Dulong et al. | |
| RE38,189 E | 7/2003 | Walker et al. | |
| 6,602,377 B1 | 8/2003 | Bar-Erez et al. | |
| 6,685,227 B2 | 2/2004 | Merry et al. | |
| 6,685,678 B2 | 2/2004 | Evans et al. | |
| 6,694,334 B2 | 2/2004 | DuLong et al. | |
| 6,915,170 B2 | 7/2005 | Engleson et al. | |
| 6,915,823 B2 | 7/2005 | Osborne et al. | |
| 6,973,435 B1 | 12/2005 | Sioufi et al. | |
| 6,976,628 B2 | 12/2005 | Krupa | |
| 6,980,111 B2 | 12/2005 | Nolte | |
| 6,985,870 B2 | 1/2006 | Martucci et al. | |
| 6,994,249 B2 | 2/2006 | Peterka et al. | |
| 7,044,664 B2 | 5/2006 | Papetti | |
| 7,074,209 B2 | 7/2006 | Evans et al. | |
| 7,111,780 B2 | 9/2006 | Broussard et al. | |
| 7,115,113 B2 | 10/2006 | Evans et al. | |
| 7,128,105 B2 | 10/2006 | Tribble et al. | |
| 7,154,397 B2 | 12/2006 | Zerhusen et al. | |
| 7,171,277 B2 | 1/2007 | Engleson et al. | |
| 7,232,066 B2 | 6/2007 | Andreasson et al. | |
| 7,236,501 B1 | 6/2007 | Lim et al. | |
| 7,236,936 B2 | 6/2007 | White et al. | |
| 7,236,939 B2 | 6/2007 | Chen et al. | |
| 7,471,994 B2 | 12/2008 | Ford et al. | |
| 7,506,807 B2 | 3/2009 | Durrell et al. | |
| 7,813,939 B2* | 10/2010 | Clements et al. | 705/2 |
| 7,918,830 B2* | 4/2011 | Langan et al. | 604/189 |
| 2002/0099334 A1 | 7/2002 | Hanson et al. | |
| 2003/0065537 A1 | 4/2003 | Evans | |
| 2005/0101905 A1 | 5/2005 | Merry | |
| 2006/0253346 A1* | 11/2006 | Gomez | 705/28 |
| 2007/0187475 A1 | 8/2007 | MacLeod | |
| 2008/0019494 A1 | 1/2008 | Toda | |
| 2008/0059228 A1* | 3/2008 | Bossi et al. | 705/2 |
| 2008/0164272 A1 | 7/2008 | Dallman | |
| 2008/0164273 A1 | 7/2008 | Dallman | |
| 2008/0314978 A1* | 12/2008 | Fedorko et al. | 235/385 |

OTHER PUBLICATIONS

Bates, "The road to implementation of the electronic health record," Baylor University Medical Center Proceedings 19(4):311-312 (2006).

Cooper et al., "An Analysis of Major Errors and Equipment Failures in Anesthesia Management: Considerations for Prevention and Detection," Anesthesiology 60:34-42 (1984).

Fasting and Gisvold, "Reports of Investigation—Adverse drug errors in anesthesia, and the impact of coloured syringe labels," Can. J. Anesth. 47(11):1060-1067 (2000).

Garnerin et al., "Drug selection errors in relation to medication labels: a simulation study," Anaesthesia 62:1090-1094 (2007).

Evans, "Comment Regarding Requirement for Drug Barcode Labeling," DocuSys Ltd., Jun. 2, 2003, retrieved from the Internet on Mar. 4, 2010 at http://www.fda.gov/OHRMS/DOCKETS/dailys/03/Jun03/062403/02N-0204_emc-000199-01.doc.

Levine et al., ""Smart Labels"—Improving Medication Safety in the Perioperative Environment," ASA Annual Meeting A759, 109 (2008).

Lexi-Comp Online interface, retrieved from the Internet on Mar. 24, 2010 at http://www.lexi.com/institutions/products/online/.

Merry and Webster, "Anaesthetists and Drug Administration Error—Towards an Irreducible Minimum," J. Australasian Anaesthesia pp. 53-61 (1996).

Miller and Sim, "Physicians' Use of Electronic Medical Records: Barriers and Solutions," Health Aff (Millwood) 23:116-126 (2004).

Nanji et al., "Smart Labels: Improving Syringe Labeling Efficiency and Accuracy in the Operating Room," Department of Anesthesia, Critical Care and Pain Medicine, Massachusetts General Hospital, Boston, MA—Poster 2009.

National Drug Code Directory interface, retrieved from the Internet on Mar. 24, 2010 at http://www.accessdata.fda.gov/scripts/cder/ndc/default.cfm.

Neuenschwander, "Practical Guide to Bar Coding for Patient Medication Safety," American Journal of Health-System Pharmacists 60:768-779 (2003).

Orser et al., "Medication errors in anesthetic practice: a survey of 687 practitioners," Canadian Journal of Anesthesia 48(2):139-146 (2001).

Poon et al., "Assessing the level of healthcare information technology adoption in the United States: a snapshot," BMC Medical Informatics and Decision Making 6:1 (2006).

Schreiner MediPharm document, "Xyringe Label," [date unknown].

The official newsletter of the Joint Commission, "The Joint Commission Perspectives," 28(2) (2008).

Vernest et al., "Smart Labels: Improving Syringe Labeling Compliance and Patient Safety in the Operating Room," Department of Anesthesia, Critical Care and Pain Medicine, Massachussetts General Hospital, Boston, MA; Department of Anesthesia, NorthShore University HealthSystem, Evanston, IL—Poster 2009.

Webster et al., "The Frequency and Nature of Drug Administration Error During Anaesthesia," Anaesth Intensive Care, 29(5):494-500 (2001).

Webster CS., "Editorial—The iatrogenic-harm cost equation and new technology," Anaesthesia 60:843-846 (2005).

* cited by examiner

DRUG LABELING

TECHNICAL FIELD

This disclosure relates to systems and methods for providing labeling for drug containers.

BACKGROUND

Drugs, such as anesthetics, are sometimes mixed and administered to patients at the point of care. For example, in operating rooms, anesthesiologists often transfer drugs from an original container to a second container, e.g. a syringe, for administration to patients and they can also dilute a drug from a concentrated form to a less concentrated form for administration to a particular patient. Regulations and standards of good practice require the prepared drug be labeled with information such as the drug name, its concentration, who prepared it, and the date/time of its creation and expiration. The labels can be color coded based on a standard color coding scheme promulgated by the American Society of Anesthesiologists (ASA) to help physicians quickly identify the type of drug that is in a container, for example, a syringe, during busy or emergency situations.

Other materials including, for example, stock chemicals in a medical laboratory or hazardous waste being transported or stored also require labels in which standard colors and/or symbols have specific meanings.

SUMMARY

This invention is based, at least in part, on the discovery of new systems and methods that significantly enhance the safety and speed of the transfer of a drug from a first container, e.g., a multi-dose, large volume container, to a second container, e.g., an individual dose container, such as a syringe or IV bag. The new systems and methods accomplish this safe and efficient transfer by not only identifying the drug in the first drug container, but also by automatically retrieving multiple drug attributes from a site-specific database and applying one or more predetermined rules to values associated with the attributes to automatically produce markings on, for example, drug labels, that include critical safety and handling information regarding the drug.

In one aspect, the invention features systems for enabling transfer of a drug from a first drug container to a second drug container. These systems include a drug identification component that retrieves drug identifying data for a drug in a first drug container, e.g., by scanning the container; a storage medium that stores a site-specific database including attributes and associated values for a set of drugs including the drug in the first drug container; a processor that obtains the drug identifying data and the attributes and associated values for the drug and produces information about the drug using the drug identifying data and the attributes and associated values; a rules engine that applies one or more rules to the information about the drug to generate drug handling information; and an output unit that outputs markings that include the drug handling information in human-readable or machine-readable form, or both, to be associated with the second container.

In various embodiments of these systems, the drug identifying data can be based on a National Drug Code (NDC) number or one or more proprietary codes. In some embodiments, the drug identifying data is derived from a barcode affixed to or on the first drug container, from an image of the first drug container, or from a radio frequency identification (RFID) tag associated with the first drug container. In these systems, the processor can communicate with a memory and the storage medium storing the site-specific database, wherein one or both of the memory and the storage medium are local to, or remote from, the system.

In some embodiments, the markings are included on a data carrier for affixing on a syringe, on a vial, or on an intravenous administration container, and the markings can include information for controlling an intravenous pump or other drug delivery device. In various embodiments, the rules can include one or more of mixing rules, diluting rules, and reconstituting rules, and the rules can include rules for intercepting recalled, expired, or prohibited drugs, or for drug interactions or drug allergies. The markings can also include information about the pedigree of a drug, or one or more of a warning that the drug contains a paralyzing agent, a warning that the drug contains latex, a warning that the drug should be protected from light, and a warning that the drug should be administered directly into a muscle. The markings can also include information enabling documentation of drug administration.

In other embodiments, the markings can include information enabling a safety system to, based on the information, provide feedback to a clinician regarding one or more of a drug name, an allergic reaction to the drug, a drug amount, and an expiration date, and/or information enabling a documentation system to, based on the information, document administration of the drug.

The systems described herein can optionally include one or more audio-visual units for producing one or more of an audible and visual indication of information about the drug.

In another aspect, the invention features systems to record the utilization of a drug transferred from a first drug container to a second drug container. These systems include a drug identification component that retrieves drug identifying data for a drug in a first container, e.g. by scanning the container; a storage medium that stores a site-specific database including attributes and associated values for a set of drugs including the drug in the first drug container; and a processor that obtains the drug identifying data and the attributes and associated values for the drug, and using the drug identifying data and the attributes and associated values, records information regarding the transfer of the drug and administration of the drug into an information management system.

In these systems, the information management system can be an anesthesia information management system. In some embodiments, one or more of the information regarding the transfer of the drug and the information regarding administration of the drug can include a name of the drug, the concentration of the drug, the NDC number of the drug, the drug lot number of the drug, and/or the identity of the person that transferred the drug.

In various embodiments, information regarding drug utilization documentation can be used to track one or more of the utilization and waste of the drug by clinicians.

In another aspect, the invention also features methods for enabling the transfer of a drug from a first drug container to a second drug container. These methods include retrieving drug identifying data for a drug in a first drug container; retrieving from a storage medium that stores a site-specific database one or more attributes and associated values for the identified drug; based on the drug identifying data and the attributes and associated values for the drug, producing, by a processor, information about the drug; applying, by a processor, one or more rules to the information about the drug to generate drug handling information; and producing markings including the drug handling information in human-readable or machine-readable form, or both, to be associated with the second container.

In another aspect, the invention features a computer program product stored on a computer readable storage device for enabling transfer of a drug from a first drug container to a second drug container, the computer program product including instructions to cause a computer to retrieve drug identifying data for a drug in a first container; retrieve from a storage medium that stores a site-specific database one or more attributes and associated values for the drug; obtain the drug identifying data and the attributes and associated values for the drug and produce information about the drug using the drug identifying data and the attributes and associated values; apply one or more rules to the information about the drug to generate drug handling information; and output markings including the drug handling information in human-readable or machine-readable form, or both, to be associated with the second container.

The invention provides several advantages. For example, the invention helps ensure patient safety by enabling clinicians to automatically produce labels for e.g., drug syringes having human readable information, and optionally machine-readable information, conforming to a hospital's safe practices and/or regulatory requirements, thus reducing the likelihood of administration errors.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
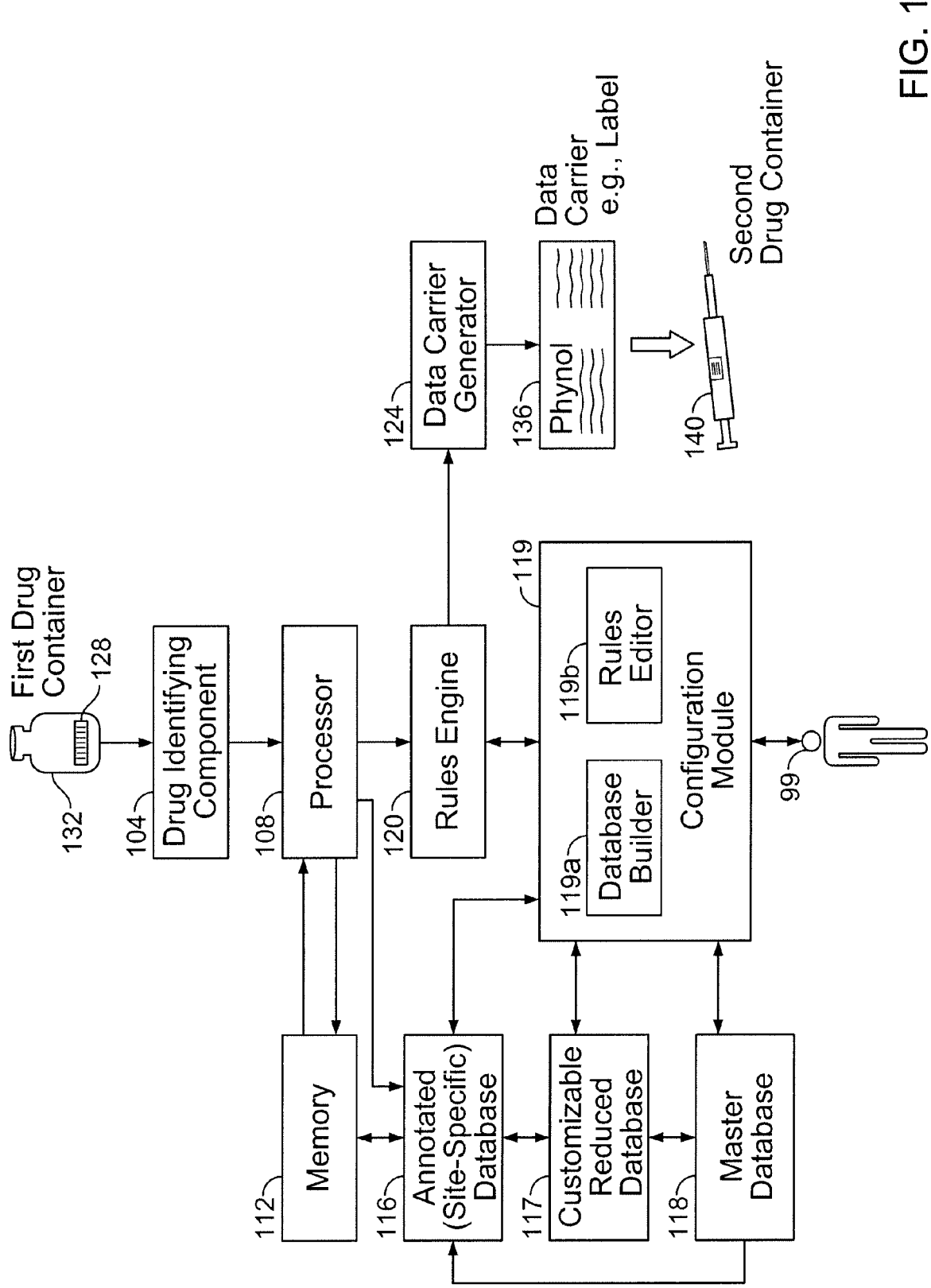
FIG. 1 is a schematic block diagram of a drug labeling system.

Disclosed are automated labeling systems and methods that can assist in accurately, quickly, and safely transferring drugs from a first drug container, e.g., a large, multi-dose container, to a second drug container, e.g., a single-dose syringe or IV bag, in, for example, a health care institution. In one implementation, the new labeling systems can obtain drug identifying data, e.g., an identity of the drug in the first container, and bind or connect, e.g., physically or electronically link, the drug identifying data with other information about the drug (referred to herein as "drug attributes"), including information about recalls of specific drugs, allergic reactions associated with particular drugs or typical diluents used with those drugs, the transfer of the drug, e.g., identity of the person performing the transfer, time of the transfer, whether the drug was diluted or mixed with one or more diluents, and an expiration date and/or time. In some examples, the labeling system can, based on the drug identifying data, retrieve the drug attributes from a local or remotely connected site-specific database.

In certain implementations, the systems can apply rules and/or guidance based on specific values of the drug attributes and/or on other contextual information, such as information about the class or category of the patient, e.g., adult, adolescent, child, or male or female, or information about the specific patient, e.g., weight, age, other health issues, or allergies. These rules can be defined by an authorized user, e.g., a clinician on behalf of the health care institution. The system can automatically produce markings on, for example, a data carrier such as a colored label, with human-readable information and/or machine-readable information that includes some or all of the appropriate information described above. In some examples, the system can produce markings with the human-readable information and/or machine-readable information that are directly printed or etched on the second drug container.

Sometimes drugs need to be diluted before they are administered. Accordingly, the labeling system can implement a drug dilution process for including information regarding the drug dilution on the labels. In some cases two or more drugs may need to be mixed in a second drug container. As such, the labeling system can implement a drug mixing process or protocol including information regarding the drug mixture on the label 136. In some implementations, the labeling system can also track the administration of the drug to a specific patient, and record the information in, e.g., a drug tracking system.

Drug Labeling

During the course of caring for a patient in a hospital it is common that a drug needs to be given to the patient. For example, a drug may need to be injected, e.g., intravenously or intramuscularly, using a syringe. In some cases, the syringe is prepackaged in a single-dose, ready-to-use, syringe configuration—in these cases the drug may not need to be transferred from a source drug container to the syringe by a clinician or at the hospital. However, in some cases, the drug may need to be transferred, mixed, reconstituted, diluted, or otherwise prepared for a patient, e.g., at the point of care. Such drug preparation is particularly common during surgery and other invasive procedures, where the anesthesiologist or nurse is constantly administering precise amounts of various drugs to ensure the patient is properly anesthetized or sedated yet not physiologically compromised.

The drug preparation can also occur in the Post-anesthesia Care Unit (PACU), the Intensive Care Unit (ICU), procedural sedation area and/or other areas of the hospital where patients need specialized drugs. Finally, in less urgent situations, an order can be written for a certain drug for a specific patient and a similar drug preparation process can also occur in a pharmacy (e.g., inside or outside a hospital), using, e.g., sophisticated labeling systems that are already part of the pharmacy infrastructure. The patient-specific drug can then be transported to the patient for administration.

Due to rigorous procedures executed by a relatively small number of highly trained technicians, most hospital and pharmacies abide by safe practices and regulatory requirements that provide for relevant information regarding a drug to be accurately and completely documented on a label affixed on a drug container. For example, if a drug is to be prepared and/or diluted and then administered to a patient via a syringe, at least the following information can be captured on a label to be affixed to the syringe: drug name, concentration, dose units, time and date of preparation and/or dilution, who prepared it, and expiration date and time. Other drug attributes may also be captured, including, but not limited to, the drug's lot number, warnings, and manufacturer or a color code to rapidly identify the classification of drug. In some examples, the minimum information that is required on a drug label may be prescribed by an industry regulatory body such as, The Joint Commission (TJC), an independent, not-for-profit organization that accredits and certifies health care organizations and programs in the United States. The Joint Commission's 2010 National Patient Safety Goals (NPSG) Mar. 4, 2001, the contents of which are incorporated by reference herein in its entirety, prescribe that in perioperative and other procedural settings both on and off the sterile field, medication or solution labels should include the following: medication name, strength, quantity, diluent and volume (if not apparent from the container), preparation date, expiration date when not used within 24 hours, and expiration time when expiration occurs in less than 24 hours.

At present, the information is typically hand-written on a blank label that is then affixed on the second container, e.g., a syringe, by the clinician who prepares the drug. In some examples, a colored label can be used to rapidly identify the classification of drug. The American Society of Anesthesiologists (ASA) standards specify twelve different classes of drugs and with corresponding color labels. For example, ASA standards require drugs that cause neuromuscular blockade to have a red label. In addition, health care settings are generally required by law to have complex requirements for tracking the disposition of narcotics and other drugs with high addiction potential.

In some cases, compliance with the safe practices and regulatory requirements outlined above can be sporadic. For example, the information on the label may be handwritten and thus prone to, for example, poor legibility and/or ink smudging. In addition, human-created handwritten labels are prone to errors. Further, the label may have only a portion of the information required by the standards, e.g., only a name of a drug and/or a concentration of the drug. Also, because the diameter of syringes can vary from being very small (e.g., 0.25") to very large (e.g., 1.25"), the labels can correspondingly vary in size. Consequently, the format of the information contained on the labels for the different may not be consistent. Further, syringes may include markings or graduations that are helpful in measuring an amount of the drug being administered. These markings or graduations generally cannot be obscured by affixing a label.

Moreover, as described above, a label can include several, e.g., twelve, different color options used for identifying drugs. Accordingly, there can be at least twelve different types of blank labels that must be kept in stock. These label stocks can takes up a lot of room on a drug cart. Electronic documentation of medicinal drug administration can be done using e.g., a bar code scanner accessory, an anesthesia information management system, an electronic medical record or other documentation system. In such systems, rolls of labels can be inconvenient as they generally cannot easily be each provided with a unique barcode with all data elements that can be useful to capture during the electronic documentation.

Automated Drug Labeling System

FIG. 1 shows one example of a drug labeling system 100, which includes a drug identifying component 104, a processor 108 in communication with a memory 112 and a database 116, a rules engine 120, and an output unit, e.g., a data carrier generator 124. In one implementation, an industrial design of the labeling system 100 can be aimed at minimizing overall size for easy placement on or near a medication cart in an operating room of a hospital. For example, the design can provide for easy cleaning and disinfection between operating room procedures as required in many hospital environments. The labeling system 100 can be implemented through the use of, for example, a workflow aware connectivity (WAC) system described in PCT Application No. PCT/US2008/079487 to Nathaniel M. Sims et. al., the content of which is incorporated herein by reference in its entirety.

In one implementation, the drug identifying component 104, e.g., a bar code laser scanner, scans or images a machine-readable identifier 128, e.g., a barcode, an RFID tag, or an image of or on, e.g., a first container 132 of a medicinal drug to retrieve, e.g., obtain, drug identifying data. The drug identifying component 104 implements a process for recognizing (e.g., identifying, scanning, and/or imaging) the first container 132 to retrieve the drug identifying data. For example, the drug container 132 can be a drug vial in, for example, an operating room. The processor 108 processes the drug identifying data to identify the drug and/or look-up other information, e.g., attributes, regarding the drug in a database, e.g., a site-specific database, 116. In this manner, the processor 108 uses the drug identifying data to retrieve other information regarding the drug from one or more local and/or remote databases 116-118.

In one implementation, the database 116 is an annotated, site-specific database that includes one or more attributes and corresponding values for a set of drugs selected from a master database 118 and/or from a reduced database 117 by a healthcare institution (e.g., via database builder 119a). The site-specific database 116 is so named, because each site (e.g., hospital or other healthcare office or institution) that uses one of the systems described herein will have its own database that is annotated specifically for that site. The set of drugs within the annotated site-specific database 116 can be selected to be representative of the range of drugs that physicians within the health care institution might wish to prescribe in their practices, and/or drugs are typically used by on-site pharmacies. The attributes are generated by the specific institution, and include safety issues and warnings (e.g., recall notices, potential allergen notices, and minimum and maximum permissible dosages and rates of administration for infusions and/or bolus amounts) as well as policy issues (e.g., use of particular types or brands of drugs compared to others or based on current inventory). In addition, some or all of the attributes in such an annotated site-specific database 116 can be updateable or customizable annotations, e.g., additional attributes and corresponding values for the selected set of drugs, such as, one or more data elements, drug policies, drug handling guidance, and/or drug status information.

The master database 118, from which the site-specific database 116 is directly or indirectly derived, can be a formulary database hosted by, for example, a third party entity such a governmental agency or industry-standard body. For example, the master database 118 can be one or more databases provided by Lexi-Comp of Hudson, Ohio or FirstDataBank of San Bruno, Calif. An example of a governmental agency database is the U.S. Food and Drug Administration (FDA)'s National Drug Code Directory.

In one implementation, a reduced database 117 can be implemented for storing a customized drug list based on some or all of the information about the drugs retrieved from the master database 118. The reduced database 117 can be located locally, e.g., physically located at the healthcare institution, or located remotely, e.g., physically located remote from the healthcare institution. The customized drug list may include some or all of the attributes from the master database 118. In such an implementation, the annotated, site-specific database 116 can be implemented based the customized drug list in the reduced database 117, along with the customizable annotations as described above.

The annotated database 116 and/or the reduced database 117 can be stored on disk storage media as files, or secured files, e.g. encrypted files, or in a memory within the system. In some examples, the files can include one or more annotated drug lists and/or customized drug lists that are stored as separate files on the disk storage media Once the processor 108 produces the information about the drug, the rules engine 120 can apply one or more rules to the information as described in detail below to generate drug handling information such as, e.g., guidance to a user of the drug, including, checking for recalls, information about allergies and/or interactions with other drugs, dosage information, warnings and other information of interest regarding the drug.

In general, the rules implemented by the rules engine 120 specify how the system 100 interacts with a user (e.g., a doctor, physician's assistant, or nurse) after the drug container 132 has been scanned. In one implementation, the rules act on the values assigned to attributes in a database, for example, the annotated database 116, by the healthcare institution. In this regard, the attributes are predetermined attributes and the healthcare institution may select values for one or more of the attributes in specifying the behavior of the system 100 through the rules. In some implementations, the attributes can be further configured by creating one or more new attributes and/or editing the existing attributes.

The rules engine 120 can be implemented as a software module executed by the processor 108. In some examples, the rules engine 120 can be implemented by a computer system that is separate from the processor 108. A drug-specific data carrier, e.g., label 136, can be produced that includes markings conforming to current best-practices and regulatory guidelines and includes at a minimum, e.g., the drug name, dose, concentration, lot number, preparation date and time, dilution date and time (if diluted), expiration date and time, clinician, pharmacist, technician or other personnel who prepared and/or transferred or mixed the drug(s), drug pedigree, color markings, drug classification indications, and/or other information such as warnings and other indications. Drug pedigree information can include, for example, a statement of origin that identifies one or more of each prior sale, purchase, or trade of a drug, including date of transactions and names and addresses of parties to the transactions. The label 136 can include human- and/or machine-readable markings. In some scenarios, e.g., during surgery, the drug is removed from a first drug container 132 and transferred to a second drug container 140, e.g., a syringe, a medicinal bowl or basin, or an IV bag. The label 136 described above can be applied to the second container 140 after information about the drug is identified and the drug is removed from the first container 132 and transferred to the second container 140.

Further, in some examples, the machine-readable portion of the label 136 can be read back into the patient's record when the drug is actually given. For example, during surgery, the drugs can be mixed before the surgery begins and administered to the patient in small amounts as the surgery progresses. In this regard, the labels' 136 machine readable markings can be scanned by, e.g., an anesthesia information management system (AIMS) or other documentation system to be recorded in e.g., the patient's medical record even as the drug is administered. This allows for an accurate and timely documentation of a drug's administration. Further, such practices can improve regulatory compliance and medication safety, and reduce drug administration errors.

Configuration Module

The drug labeling system 100 can include a configuration module 119 having a database builder 119a and a rules editor 119b. In one implementation, the configuration module 119 can be implemented as a software application program executed by the processor 108. In some examples, the configuration module 119 can be implemented by a computer system that is separate the processor 108. Further, it should be recognized that, in some examples, the database builder 119a can be implemented by a first computer system, and the rules editor 119b can be implemented by another computer system.

The database builder 119a can provide a user interface (for example, FIG. 1C) for enabling an authorized individual 99 (e.g., a user with an authorized password and access level) to, for example, retrieve information about one or more drugs from the master database 118, and specify additional attributes, such as, fields (columns) having values to be stored in the annotated database 116.

In one implementation, using the database builder 119a, the authorized individual 99 can process the information retrieved from the master database 118 into a smaller and customized drug list having one or more predetermined attributes (described in further detail below). This customized drug list can be stored in the reduced database 117. Further, the authorized individual 99 can annotate the customized drug list with additional information about the drugs and store the annotated list in the annotated database 116. The database builder 119a enables the authorized individual 99 to easily construct entries for the annotated database 116 and/or the reduced database 117 both by selecting particular drug entries from the master database 118 and/or by creating custom drug entries. Once the annotated database 116 and/or the customizable reduced database 117 has been constructed, the database builder 119a can enable the authorized individual 99 to download the annotated database 116 and/or the reduced database 117 into one or more handheld devices (e.g., handheld device 1 in FIG. 2 below) for use in identifying and processing drugs in the drug containers 132.

In one implementation, the media on which the annotated database 116 and/or the reduced database 117 is stored can also include a user file that contains, for example, a full name, a password and an authorized access level for one or more authorized individuals 99 that are authorized to access the functionality of the configuration module 119. Further, in one implementation, for tracing and accountability purposes, the configuration module 119 can include a track log for storing information about changes made to the annotated database 116 and/or the reduced database 117 along with identifying information of the authorized individual 99 who made the changes.

Figure 1B:
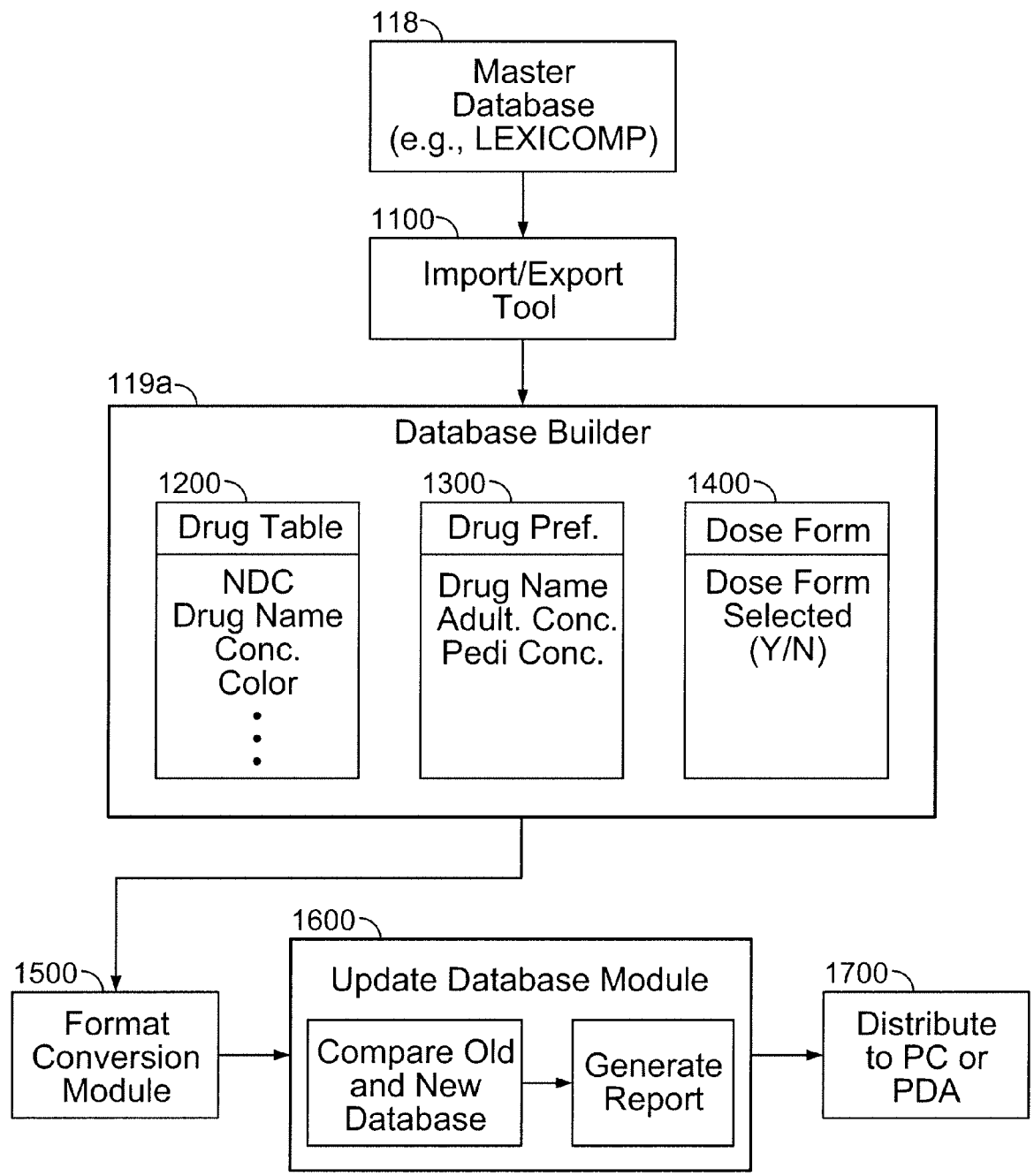
FIG. 1B is a schematic block diagram of a database builder.
Figure 7:
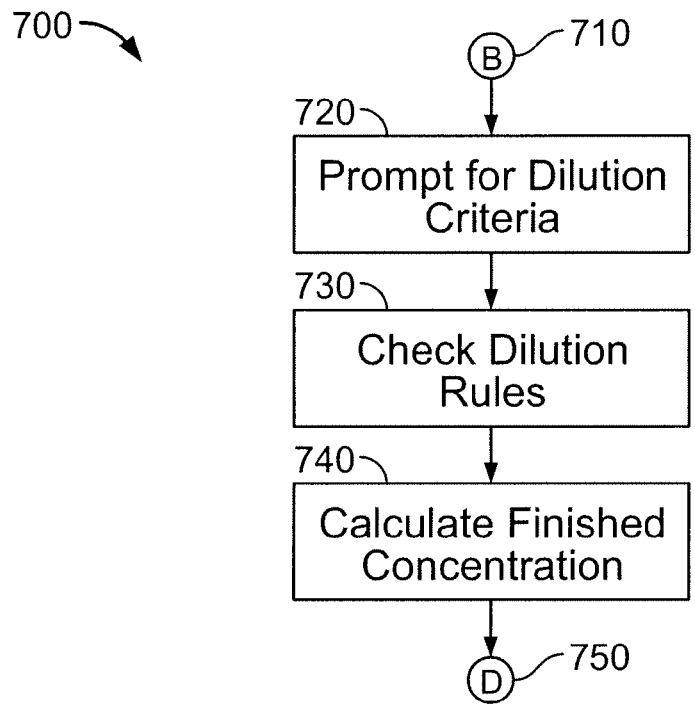
FIG. 7 is a flowchart showing a drug dilution subroutine.

FIG. 1B shows an example schematic for extracting drug information from a master database 118, e.g., Lexi-Comp of Hudson, Ohio. In one implementation, the master database 118 can be implemented in Microsoft Access format. Accordingly, an import/export tool 1100 can be used to convert the database format into a native format, for example, SQL Server database format. The import/export tool 1100 can access the master database 118 using any transfer protocol, for example, file transfer protocol (FTP). The database builder 119a can then be used to view tables that have been automatically populated based on attributes and values contained in the tables of the master database 118 (e.g., Drug table 1200). Using the database builder 119a, an authorized individual 99 can specify a new "dataset" that includes, for example, the Drug table 1200 and one or more new tables and attributes and associated values (e.g., Drug Preferences table 1300 and Dose Form table 1400). These new tables along with the attributes and associated values can be stored in, for example, the annotated database 116 (FIG. 7).

The annotated database 116 can be changed to a format that is acceptable to the destination environment where the database 116 would be uploaded, e.g., a computer system or a personal digital assistant (PDA). For example, in the format conversion module 1500, the information in the annotated database 116 can be converted into a format supported by Microsoft Excel, which can then be converted into a file having comma separated values. In one implementation, the annotated database 116 can be directly converted into the file having comma separated values. In an update database module 1600, the database builder 119a can check to see if the changes that have been made to the tables corresponding to the annotated database 116 call for replacing the tables in an old annotated database with a new annotated database. In such an implementation, when the old database is replaced with the new database, a change report can be generated that documents the changes. Finally, a distribution module 1700 can assist in uploading the changed annotated database 1700 to the computer system or the PDA.

Figure 1C:
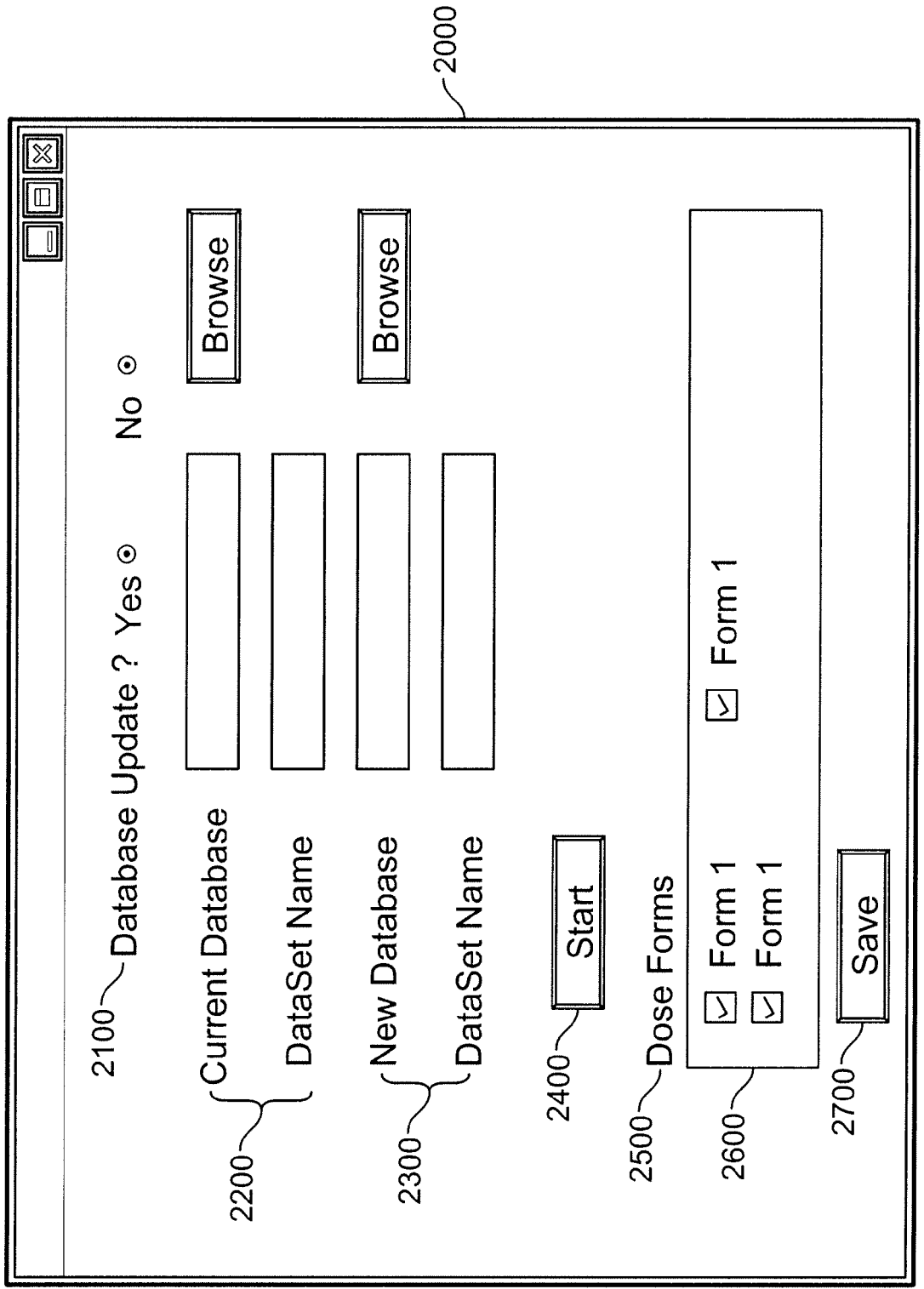
FIG. 1C is a representation of a screenshot from the database builder.

FIG. 1C shows an example user interface 2000 implemented by the database builder 119a. Field "Database update?" 2100 is used to indicate whether a database update is expected. If the old database is to be replaced by a new database, the radio button "Yes" is checked. Fields "Current database" and "Data Set name" 2200 can be used to specify a location of the current database and a data set within the database that is to be updated. If the current database is to be replaced by a new database, fields "New Database" and "Data Set name" 2300 can be used to specify the location and name of the new database and data set within the new database. If the new data set name matches an existing data set name, the existing data set is overwritten by the new data set. Once the information in fields 2100-2300 is provided, the "start" button 2400 can be activated to begin the update process described above, and dose forms information 2500-2600 is displayed.

In one implementation, dose forms corresponding to the drugs in the database can be provided through item "Dose Forms" 2500 on the user interface 2000. If an existing database is being updated, then dose forms from the existing database can be used. If a new database is replacing the existing database, then check items 2600 can present the dose forms to be associated with the drugs in the new database.

When the "Save" button 2700 is activated, the new database having the new tables (e.g., Drug table, Drug preferences table, Dose Forms table corresponding to FIG. 1B) are created. In an update of an existing database, the new database is updated with information and preferences from the existing database. If the existing database is not being updated, then information about the new drugs is added to the existing tables. For example, National Drug Code (NDC) values corresponding to the new drugs can be added to the existing tables. Subsequently, a tool, for example, a Database Verify tool (not shown) can produce a change report documenting all the differences between the current dataset and the new dataset. This report can be used to identify to the clinician 101 what drugs are new in comparison to the current dataset and any changes made to the dataset.

Rules Engine

In one implementation, the configuration module 119 includes a rules editor 119b having a user interface for enabling the authorized individual 99 to create and/or edit one or more rules to be applied to the information about the drug produced by the processor 108. The rules are implemented by the rules engine 120. The rules may be based on one or more national, regional, hospital, departmental, or patient specific rules to be applied to a drug in question. For example, if the drug Propofol at a concentration of 1000 mg/mL is identified, but the maximum concentration allowed by a hospital is 10 mg/mL, an alert can immediately be generated. The rules engine 120 can also cause the system 100 to generate a warning label having an appropriate warning message such as: "DO NOT USE—OVERDOSE HAZARD." In this scenario, other than the warning label, another option is that the system would produce no drug label 136 at all. In some examples, if the drug is identified as being on a recall list, the clinician can be alerted and a label can be produced which says: "DO NOT USE—RECALLED DRUG—RETURN TO PHARMACY." In some examples, the rules may also include one or more dilution and/or mixing rules.

The rules engine 120 can also apply rules for proper identification of drugs. For example, the American Society of Anesthesiologists specifies that, in an operating room, muscle relaxants must be labeled with a red label. Accordingly, once the rules engine 120 determines that the drug is a muscle relaxant, the rules engine 120 can instruct the data carrier generator 124 (FIG. 1) to, e.g., produce a red label.

In some examples, user-defined rules can be agreed upon by, for example, a therapeutics committee authorized by the healthcare institution to create rules on behalf of the institution. The rules can then be entered into the rules editor 119b by the authorized individual 99 e.g., system administrator.

The institution (or the therapeutics committee acting on behalf of the institution) may authorize a master set of drugs for use in a specific site (e.g., operating room) within the institution. Optionally, the institution may further authorize one or more subsets of drugs that are derived from the master set of drugs for specific applications (e.g. drugs for one or more of pediatric, cardiac, and/or pregnancy applications).

In some examples, the master set of drugs can be organized into a hierarchy having multiple levels. As such, the institution can create a classification of the site-specific drugs. Each classification can define one or more of the following associated attributes. The authorized individual 99 can create rules for drugs by assigning values to these attributes.

1) Text Attributes, i.e., Text that is to be Associated with a Drug.

The text attribute includes text that is associated with naming a drug. For example, the text "Propofol" may be used to refer to a drug. However, the drug may also be marketed as "Diprivan" by AstraZeneca Pharmaceuticals LP, Wilmington, Del. Other examples of text attributes may include, for example, a name that is to appear on user interface screens for verification, and a name that is to be printed on the label 136. The text attribute can also indicate whether the name should appear in "tall man" lettering, and/or whether any additional text should accompany the name. For example, the text "Paralyzing Agent" may accompany the name of the drug to indicate that the drug is a paralyzing agent.

2) Multimedia Attributes

For example, one or more sound files can be associated with the drug to produce audible identification and warnings.

Also, one or more graphics files and/or video files can be associated with the drug for visual identification and warnings.

3) Label Template Attributes

For example, one or more label attributes may be specified for the drug, such as, a color, a pattern, a style, a size, a graphic (e.g., a logo), a barcode type, and/or an indication of where information is to be printed on the label 136.

In some examples, the institution can also specify a set of one or more of the following attributes to be associated with each drug.

1) All subsets to which the drug belongs.
2) Classification of the drug.
3) Status attribute (e.g., an indication of whether the drug can be used. This attribute can also be used to specify whether the drug has a status of "recalled," "for adult-use only," "not-recommended," and/or "restricted").
4) Text attributes overrides (e.g., an indication of whether the text attribute associated with the drug as specified by, for example, the master database 118 can be overridden to indicate a new text attribute. For example, "Diprivan" can be labeled as "Propofol" for appearance on a user interface screen within the institution or for appearance on the label 136).
5) Multimedia attribute override (e.g., an indication of whether the multimedia attribute associated with the drug as specified by, for example, the master database 118 can be overridden to indicate a new multimedia attribute).
6) Label template attribute overrides (e.g., an indication of whether the Label template attribute associated with the drug as specified by, for example, the master database 118 can be overridden to indicate a new label template attribute).
7) Diluent attributes (an indication of whether a diluent is allowed, preferred, and/or required for the drug, e.g. distilled water, normal saline).
8) Expiration attributes (e.g., an amount of time after preparation that the drug in drug container expires).
9) Barcode attributes (e.g., information about the barcode, e.g., types of barcodes, such as, PDF-417, Datamatrix, and/or encoding standards. Also, the barcode attributes may include content of the barcodes such as a unique tracking code, and/or NDC, and/or one or more other user-defined drug attributes).

In some examples, the authorized individual 99 can use the rules editor 119b to specify one or more features for label 136. In one implementation, a bar code component that is distinct from the rules editor 119b (and located inside or outside the configuration module 119) can be used to specify the features for the bar code on label 136. For example, the rules editor 119b can allow the authorized individual to customize one or more bar code elements (e.g., 45, 55, and 55' of FIGS. 4 and 5A-B) on the label 136. The authorized individual 99 can specify the type of bar code elements (e.g., bar code symbologies) and set preferences for the type of information contained in the bar code elements (as described in detail below).

In some examples, the authorized individual 99 can use the rules editor 119b to apply rules to sections of the annotated database 116 and/or the reduced database 117. For example, the authorized user 99 can specify that all of the entries in the databases 116, 117 corresponding to a class of drugs called muscle relaxants print a red label and a warning message. As such, the authorized individual 99 can save the time of having to apply rules for each entry in the databases 116, 117, and further assure reasonably safely. In one implementation, the authorized individual 99 can use the rules editor 119b to apply rules to one or more drug entries corresponding to individual NDCs. For example, a rule can be implemented to generate a recall message for a particular drug from one specific source.

In one implementation, the rules editor 119b can produce change reports for audit checks. In some examples, the change reports can be produced by a component separate from the rules editor 119b, but take directions from the rules editor 119b. For example, a process can be implemented for comparing the reduced database 117 at a particular site to a latest monthly download from the master database 118. As described above, the site administrators (e.g., authorized individual 99), can then make updates and apply site specific rules to the reduced database 117 or the annotated database 116. In such an implementation, an additional change report can be generated for quality checks and tracking purposes. Further, the change report can be used for version control of the individual devices and compare the content of old and new databases.

Drug Scanning and Look-Up

Figure 2:
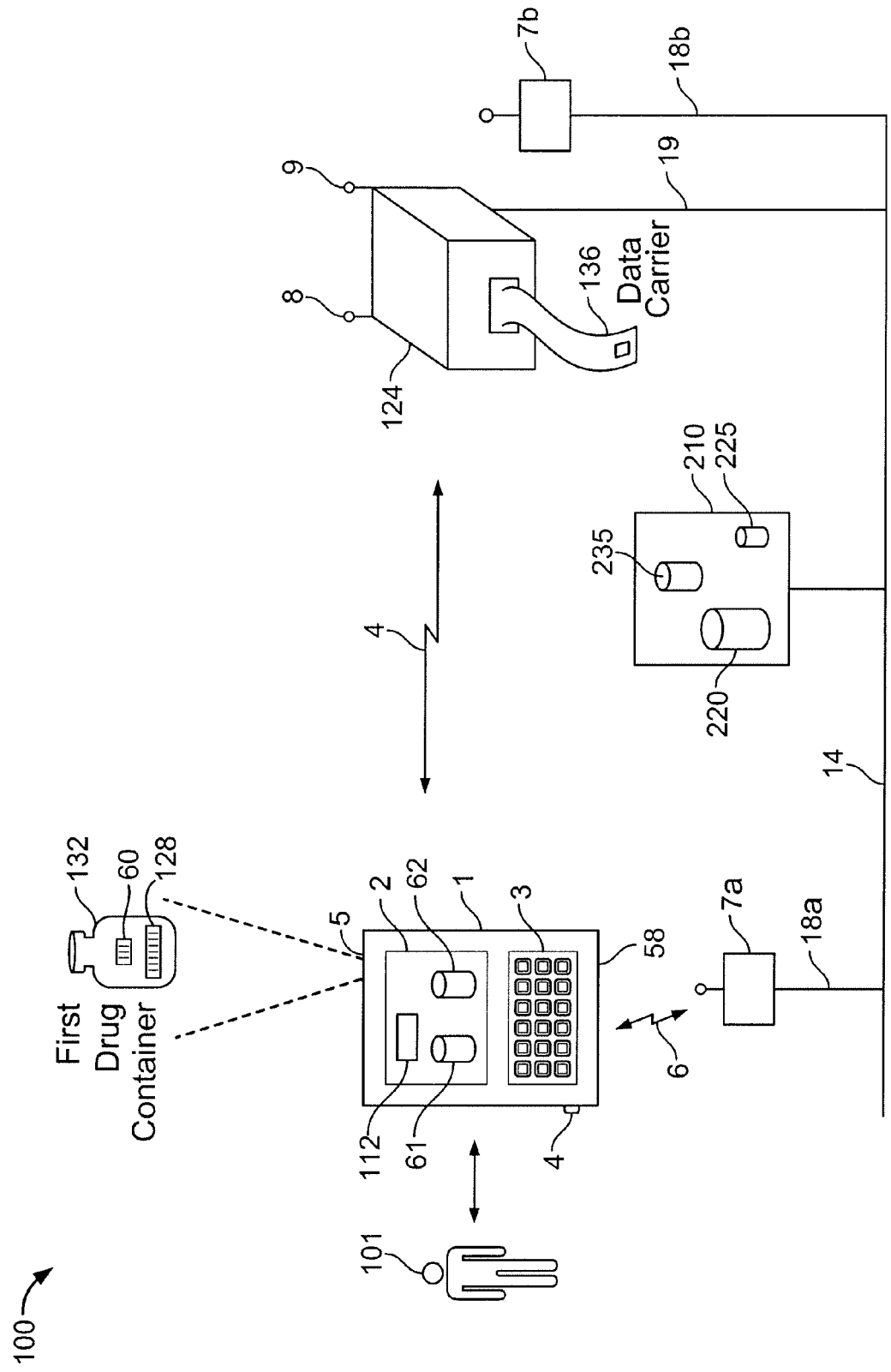
FIGS. 2 and 3 are schematic diagrams of additional implementations of the drug labeling system.

Referring to FIG. 2, in some implementations, the drug identifying component 104 (FIG. 1) can include a handheld computer 1 having a display 2 and a keyboard 3 for recognizing one or more drugs in drug containers 132. In some examples, the display 2 can include an audio-visual unit, e.g., a touch screen and/or a microphone and speaker 58 for data input. For example, the display 2 can include a back-lit, flat panel display with a touch screen. In some examples, the handheld computer 1 can be implemented within a smart phone or a personal digital assistant (PDA) that includes either circuitry in hardware or software application modules for carrying out the features of the labeling system 100. In one implementation, the handheld computer 1 can be the MC70 Handheld Mobile Computer from Motorola, Holtsville, N.Y.

The handheld computer 1 can include a built in camera/optical scanner 5 that can scan a variety of types of barcodes. The handheld computer 1 can also include a variety of radio links, e.g., a short range IEEE 802.15.1 (Bluetooth) link 4, and a longer range IEEE 802.11 (WiFi) link 6.

In some implementations, the handheld computer 1 can include a port (not shown) for accepting software updates. The software updates can be transferred to the handheld computer 1 through a wired or wireless connection. The updates can ensure update integrity and provide for reverting to a previous version manually or automatically if an error is detected during an upgrade. In some examples, multiple update package deliverable scenarios can be supported. For example, in an example, update packages can be applied individually in an appropriate order for items such as firmware updates, software application updates and/or database updates. Various methods known to those skilled in the art can be used to deliver application update packages.

A clinician 101 can use the handheld's 1 imager/scanner 5 to, e.g., scan or image the container 132 to identify the drug in the container 132. In some examples, the clinician can scan a barcode on the identifier 128, or scan an RFID tag 60 on the container 132 (or on the identifier 128), or image the container 132 and/or the identifier 128 and compare the image of the container 132 or the identifier 128 to known images in a, e.g., first database 61 located in the handheld computer 1. In some implementations, a server 210 on, e.g., a hospital computer network 14 (e.g., local area network) can include the database of known images, e.g., database 225. In such implementations, the handheld computer 1 can communicate with the database 225 on the server 210 through, e.g., long range WiFi link 6.

In one implementation, the processor 108 (FIG. 1) can be implemented in the handheld computer 1. The processor 108 in the handheld computer 1 can communicate with a memory 112, e.g., also located in the handheld computer 1. In some examples, the memory 112 can be a removable memory unit.

The handheld computer 1 can include a variety of wireless and wired communications links that allow the handheld computer 1 to communicate with e.g., the server 210 over the network 14. For example, the handheld computer 1 can transmit the drug identifying data based on, e.g., the barcode on the identifier 128, to the server 210. The server 210 can look up information about the drug based on the drug identifying data in a variety of proprietary databases, e.g., database 220. The database 220 can be local to the server 210, or the server 210 can remotely connect to one or more databases at remote locations. For example, the database 220 can be local to the server 210 and be, for example, the annotated database 116 and/or the reduced database 117 (FIG. 1). In some examples, the server 210 can directly connect to one or more remote databases that may be government agency and/or industry-standard databases, for example, the master database 118 (FIG. 1). In this regard, the drug identifying data based on the barcode on the identifier 128 can be converted into an NDC number and looked up directly in the master database 118. In some examples, if the barcode on the identifier 128 includes a hospital generated number, or a manufacturer's unique number that has been previously entered into the local database 220, then the drug information can be looked up in the database 220 with no need to connect to another remotely located database.

In some implementations, the handheld computer 1 can include a second database 62 having information about drugs that are uploaded as needed from the server 210. In one implementation, the second database 62 can be the annotated database 116 (FIG. 1). In some implementations, the database 62 on the handheld computer 1 can include information about drugs that are frequently looked up. By locating the database 62 on the handheld computer 1, the labeling system 100 may achieve higher look-up speeds, and further, the handheld computer 1 will not need to always be connected to the network 14. In this manner, the handheld computer 1 can provide improved reliability during a drug transfer process.

In some implementations, the server 210 can also include a utilization database 235 for storing drug information such as, drug name, pedigree and final concentration administered to a patient. In some examples, the utilization database 235 can be located in the handheld computer 1 and stores, for example, the last several drug administrations. The utilization database 235 can be used to produce reports describing actual drug utilization as described in the section on drug administration below.

The handheld databases 61 and 62 can be synchronized and updated with the server databases 220 and 225 through the network 14 in a variety of ways known to those skilled in the art. Once the first drug container 132 is identified, the handheld computer 1 can be configured to display a name of the drug and/or other information about the drug on the display 2. In some examples, the handheld computer 1 can announce the name of the drug and/or the other information about the drug through the speaker 58.

Figure 3:
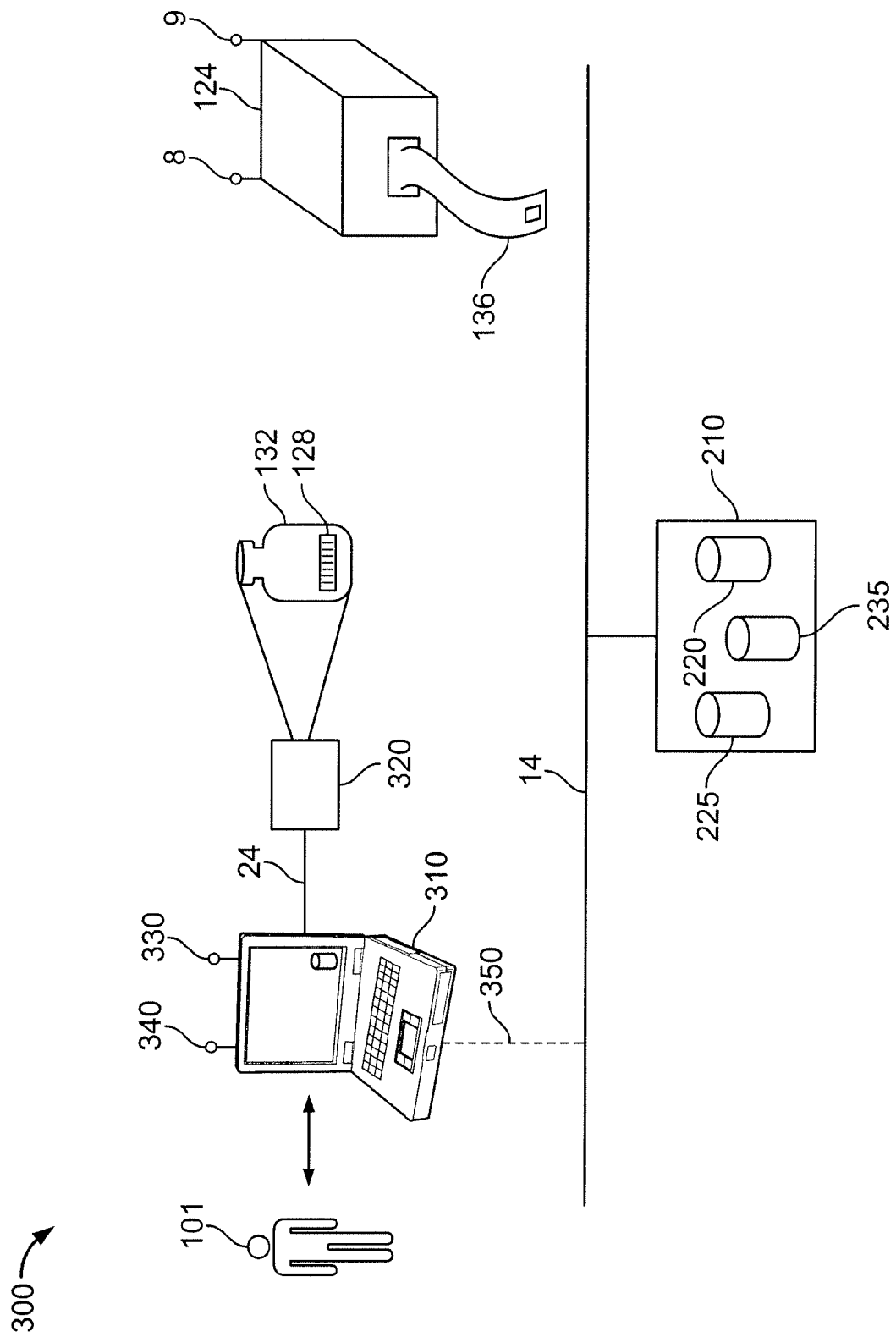

FIG. 3 illustrates a labeling system 300 that can include a desktop or laptop computer 310 in communication with an imager/scanner 320 for scanning and/or imaging drug containers 132 and/or identifiers 128 on the drug containers 132. In scenarios where a hospital is already equipped with a computer system and network, such a system 300 can be cost effective. For example, the computer 310 may already be part of an Anesthesia Information Management system (AIMS). Since computers 310 are available in most hospitals, the system 300 can be easy to setup and maintain. The computer 310 is connected via a wired or wireless link 24 to the imager/scanner 320 (having similar functionality as, e.g., the imager/scanner 5 of FIG. 1) In some implementations, the computer 310 can include short range radio links 330 and/or long range radio links 340 for connecting to e.g., server 210 on the network 14. In some examples, the computer 310 can also connect to the network 14 through e.g., wire 350. The computer 310 can include a keyboard 360 and/or one or more other input devices, and a display 370. For example, the computer 310 can be a portable computer such as the C5 provided by Motion Computing of Austin, Tex.

As described above, once the drug in the first drug container 132 is identified, the system 100, 300 can display the name of the drug and "read back" the name by, e.g., producing audible and visual feedback. The "read back" can assist e.g., a busy clinician by providing way to confirm to identify of the drug and thus reduce potential for errors. If the clinician hears or sees the wrong drug name, he or she can stop drawing up the drug before it is administer to a patient.

Label Generation

FIGS. 1-3 show that the system 100, 300 can include an output unit for producing markings including drug handling information on the label 136 and/or directly on the drug container 140. For example, the output unit can be the data carrier generator 124. In one implementation, the data carrier generator 124 can be a label printer. The data carrier generator 124 can produce a variety of types of labels 136. In some examples, the data carrier generator 124 can be configured to produce labels 136 in color. In some examples, the data carrier generator 124 can be configured to produce labels 136 in grayscale. In some implementations, the labels 136 include only machine-readable markings. Further, in some examples, as described above, the label 136 can include both human- and machine-readable markings The data carrier generator 124 can be connected to the network 14 through a hardwired connection (e.g., wired connection to local area network 14, or a local serial, USB, or parallel port connection). In some examples, the data carrier generator 124 can be connected to the network 14 through e.g., a short range wireless connection (such as IEEE 802.15.1 Bluetooth) 8 or a long range wireless connection (such as IEEE 802.11 WiFi) 9. The network 14 may include wired connections 18a or 18b to access points 7a and 7b to enable the connection of the 802.11 links into the wired network 14. In some examples, the data carrier generator 124 may be connected to the network 14 through a, e.g., wire or cable 19. The data carrier generator 124 may also connect directly to the handheld computer 1 through a short range radio link 4. Alternatively the handheld computer 1 may communicate over its long range radio link 6, through, e.g., network access points 7a, 7b, to the data carrier generator 124.

Through one or more data transfer mechanisms described above, the handheld computer 1, the desktop computer 310, and/or the server 210 can send the drug-specific information (e.g., drug name, concentration, dose units, time and date of preparation and/or dilution, who prepared the drug, and expiration date and time) for inclusion on the label 136. For example, the desktop computer 310 can communicate to a local printer serving as the data carrier generator 124 to print the label 136. In this manner, the handheld computer 1, the desktop computer 310, and/or the server 210 can cause the data carrier generator 124 to print a label 136 to be applied on the drug container 140, e.g., a syringe.

The system 100, 300 can allow for other specialty "compliance" labels to be printed, such as, intravenous insertion times and expirations as well as labels to mark invasive monitoring devices on a patient or on patient monitoring systems, e.g., central venous lines, arterial lines, and/or intracranial pressure lines.

While the new systems described herein are typically designed to generate a paper or plastic label that can be affixed to the second drug container, in some embodiments, the new systems include a device the prints, inscribes, etches, embosses, or otherwise applies the human-readable and/or machine-readable drug handling information directly onto the second container.

Label Features

Figure 4:
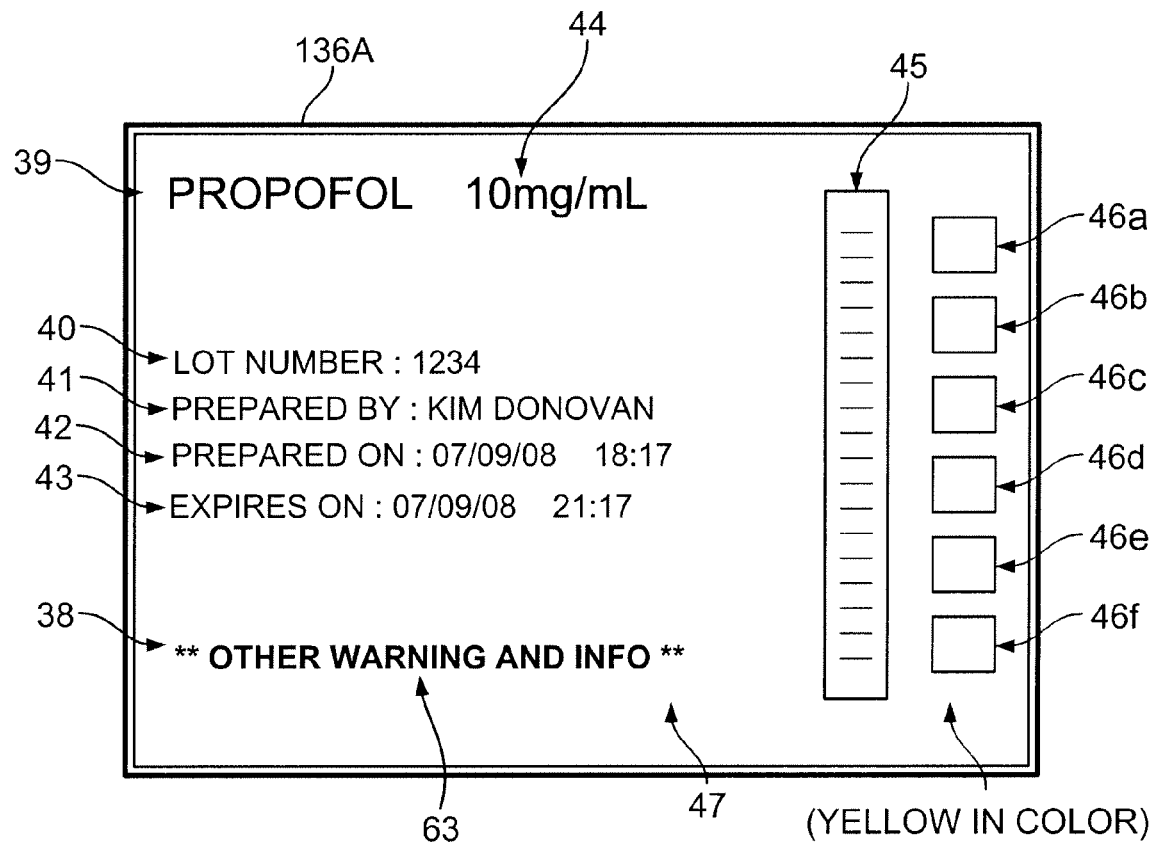
FIGS. 4 and 5A-B are schematic diagrams of different drug labels.

FIG. 4 illustrates an example of a label 136A for a drug that has not been diluted. The label 136A includes the name of the drug, e.g., "Propofol" 39, the concentration of the drug, e.g., "10 mg/mL" 44, the lot number corresponding to the drug, e.g., "1234" 40, the identity of the clinician 101 who transferred the drug, e.g., "Kim Donovan" 41, time/date stamp that the drug was transferred, e.g., "07/09/08 18:17" 42, and time/date the drug expires, e.g., "07/09/08 21:17" 43. The label 136 can also include warnings and/or other information 63.

In some examples, as described above, the background 47 of the label 136A can be colored, where the color can indicate e.g., drug classification. In other words, the label 136A itself can be colored, and the label printer adds information to the colored label 136A, or the label printer can print the colored background as well as add additional information. For example, the background 47 can be yellow to indicate that Propofol is an induction agent. The label 136A can also include a linear barcode 45 and/or one or more two-dimensional barcodes 46a-f that can be read by, e.g., an external information system and/or other medical devices. In other embodiments, the unprinted label includes various fields of all potentially required colors, and the printer is directed to print black (or white) ink to obscure all but the particular color field required for a specific drug. In this way, a single type of label can be used for any type of drug that requires a color designation, without the need for multiple different colored labels, and without the need for a color printer.

One or more small two-dimensional barcodes 46a-f can be advantageous on small syringes. Since the label 136 must wrap around the syringe, the curvature of the syringe (and hence the label 136) can cause barcodes printed on the label 136A to also have a slight curvature. As such, the barcodes are distorted making it difficult for the imager/scanner 5 to read the label 136A. By using smaller barcodes 46a-f, the effective curvature on any one barcode 46a-f is smaller and hence easier for the imager/scanner 5 to read the label 136A. In some examples, multiple barcodes 46a-f can include duplicate information or can include concatenated information and simply provide more "targets" for the imager scanner 5. This can be useful as it would allow the clinician 101 to find a barcode 46a-f easily without having to rotate the syringe.

Figure 5A:
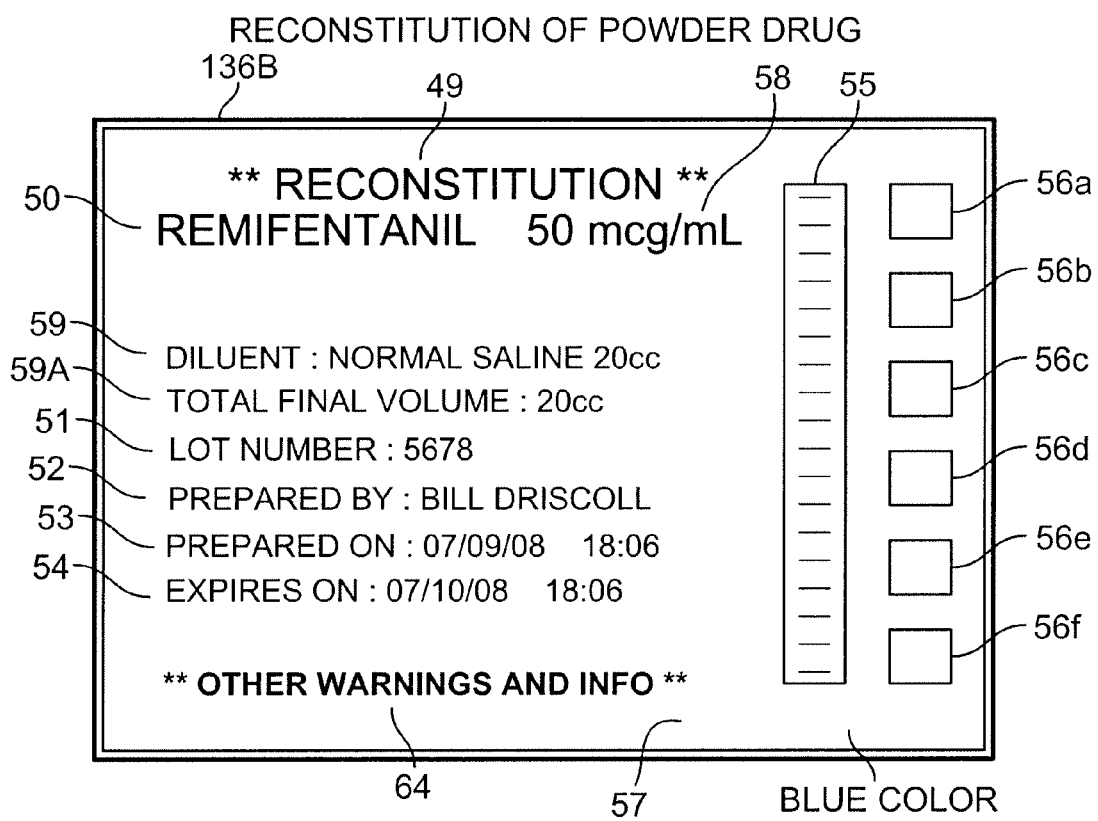

FIG. 5A shows an example of a label 136B for a drug that has been reconstituted from a powder. As shown, a cautionary message 49 can be included on a portion of the label 136B. Similar to the label 136A of FIG. 4, the label 136B can include a name of the drug, e.g., "Remifentanil" 50, and information that the drug is administered in a reconstituted concentration, e.g., "50 mcg/ml" 58. The label 136B can also include lot number, e.g., "3678" 51, identity of the clinician 101 who prepared the drug, e.g., "Bill Driscoll" 52, time/date stamp that the drug was transferred/prepared, e.g., "07/09/08 18:06" 53, and time/date the drug expires, e.g., "07/10/08 18:06" 54. The label 136B can also include information about the diluent and volume of the diluent, e.g., "Normal Saline 20 cc" 59, and information about the total final volume of the reconstituted drug, e.g., "20 cc" 59A. The label 136B can also include warnings and/or other information 64. The label 136B also has linear barcodes 55 and/or one or more two-dimensional barcodes 56a-g. In this label 136B, the background 57 may be blue for, e.g., identifying that the drug is a narcotic.

Figure 5B:
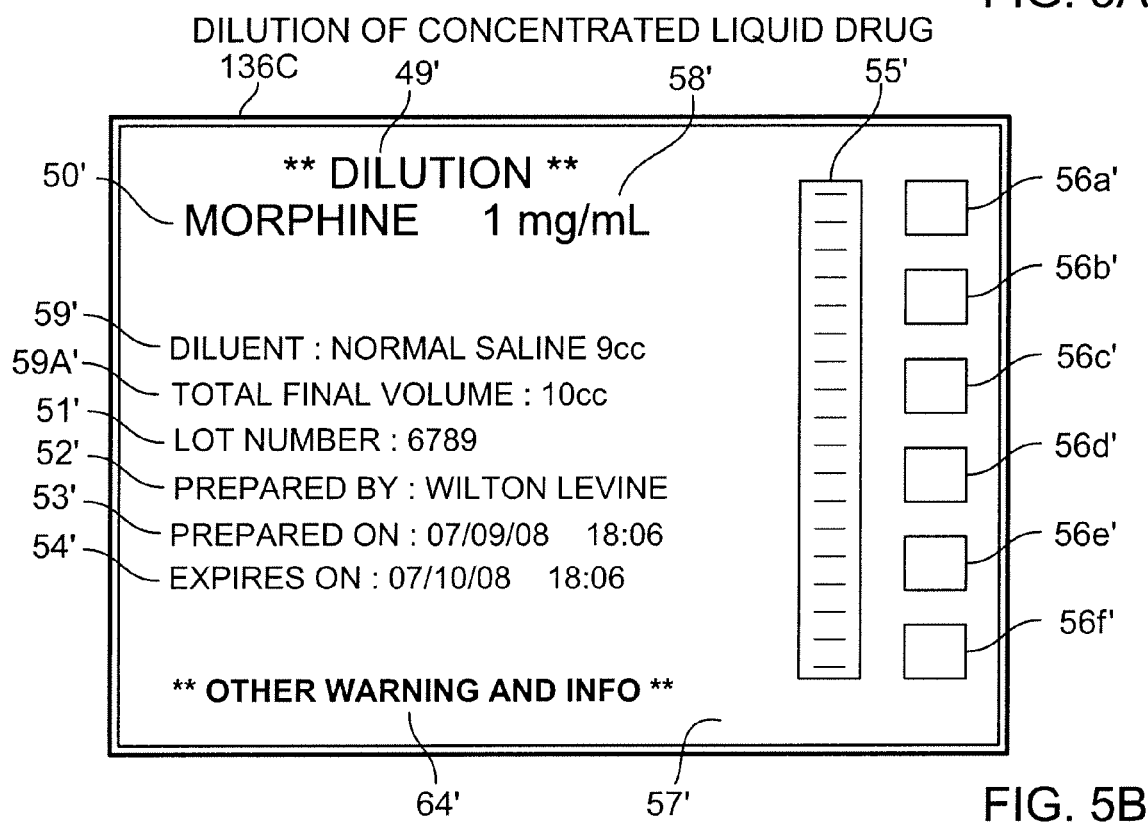

FIG. 5B shows an example of a label 136C for a drug that has been diluted from a concentrated liquid drug. A cautionary message 49' can be included on the label 136B. Similar to the label 136A of FIG. 4, the label 136C can include information about the name of the drug, e.g., "Morphine" 50', and information that the drug is administered in a diluted concentration, e.g., "1 mg/ml" 58'. The label 136C can also include information about lot number, e.g., "6789" 51', identity of the clinician 101 who prepared the drug, e.g., "Wilton Levine" 52', time/date stamp that the drug was transferred/prepared, e.g., "07/09/08 18:06" 53', and time/date the drug expires, e.g., "07/10/08 18:06" 54'. The label 136C can also include information about the diluent and volume of the diluent, e.g., "Normal Saline 9 cc" 59', and information about the total final volume of the reconstituted drug, e.g., "10 cc" 59A'. The label 136C can also include warnings and/or other information 64'. The label 136C also has linear barcodes 55' and/or one or more two-dimensional barcodes 56'a-f. In this label 136C, the background 57' may be blue for, e.g., identifying that the drug is a narcotic.

In one implementation, the labels 136A-C produced by the data carrier generator 124 and applied to syringes into which drugs are drawn are legible and water proof, and thus comply with prescribed standards. Further, clean clear labels 136A-C can enhance patient safety by reducing a likelihood of a "syringe swap."

In some examples, the information contained in the linear barcodes 45, 55, and 55', and/or the two-dimensional barcodes, 46a-f, 56a-f, and 56'a-f of FIGS. 4 and 5A-B can be decoded to a unique identifier (e.g., a string of characters) that functions as a pointer to additional information. In one implementation, the additional information can be sourced via, e.g., a networked look-up. An advantage of such a scheme is that the information object that the identifier points to can be a large object.

In some examples, the information contained in the barcodes can be based on government and/or industry prescribed standards, e.g., standards prescribed in "Positive Identification for Patient Medication Safety, ANSI/HIBC 3.0-2008," made available by the Health Industry Business Communications Council (HIBCC). The scheme for encoding the information in the bar code can be modified by an authorized individual (e.g., a system administrator) as needed for particular situations. In one implementation, the information contained in such barcodes can be decoded to the following exemplary string: "DIC/SYR/Drug name/NDC/user/exp/serialnumber/\DIC"

A destination system, e.g., an anesthesia information management system, may need to "know" certain information about the drug before the drug is administered to a patient. In this regard, the string above can provide the necessary information. As described above, an authorized individual 99 can use a software interface (e.g., rules editor 119b of FIG. 1) to specify the information in the string and thus in the bar code elements. In one implementation, the string can include the following information:

1) an identifier that identifies the item as a syringe;
2) an identifier that identifies the name of the drug (e.g., if the destination system can only use that particular drug);
3) an identifier that identifies the NDC (e.g., if the destination system can use the true source); and/or
4) an identifier that includes the identity of the clinician 101 and expiration information in a unique code format, e.g., Hex format, base 64 encoding. The identifier can be, e.g., a unique serial number that forms a portion of the string.

Using the information contained in the string above, one or more administration rules (e.g., "has this syringe been used before on a different patient?") can be run on the destination system before documenting the administration of the drug.

In one implementation, the information contained in the bar code can be parsed locally, i.e., the decoding of the bar code can be performed within the computer system (e.g., the drug identifying component 104) and/or the personal digital assistant (e.g., handheld computer 1) that scans the drug container 132 and/or the identifier 128 on the drug container 132. An advantage of such a scheme is that the information can be instantly obtained without delays or failure-modes that may be inherent in networked lookups.

Example Process for Drug Labeling

Figure 6:
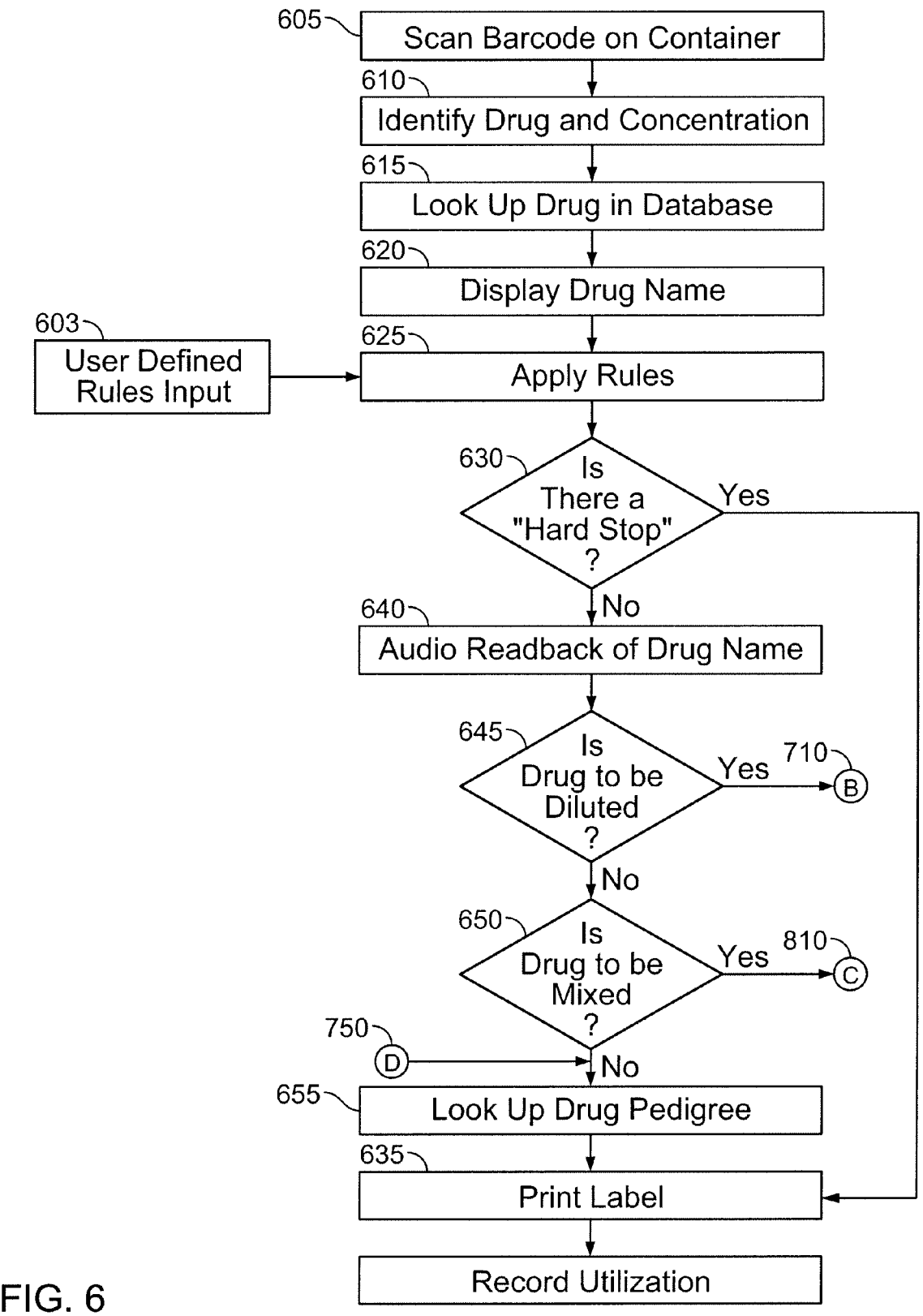
FIG. 6 is a flowchart showing a drug labeling process.

FIG. 6 shows a flowchart for an example of a drug labeling method 600. The clinician 101 first scans and or images a barcode on the label 136 and/or on the first drug container 132 (Step 605). The drug and possibly other information, e.g., drug concentration, is identified as drug identifying data (Step 610). Based on the drug identifying data, a local or remote database, e.g., database 62 and/or database 220 is looked-up to produce information about the drug (Step 615). In some examples, the drug name can be displayed to the clinician 101 (Step 620). In some examples, the drug concentration and/or other information regarding the drug can be displayed to the clinician 101. Subsequently, one or more rules, e.g., user-generated rules 503, that are based on compliance and safety standards are applied (Step 625). For example, if there is a "hard stop," such as when a recalled drug is identified (Step 630), the clinician may not be able to continue the process of producing a drug label 136, and may instead be directed to producing a label 136 having only warning messages (Steps 635). Otherwise, in some implementations, the drug name or other information can be announced over a speaker 58 (Step 640). In some examples, the warning messages can also be played over the speaker 58.

In some examples, a drug may need to be diluted as described in further detail below (Step 645). If there is no need for dilution, in some examples, a drug may need to be mixed as also described in detail below (Step 650). In some examples, the clinician 101 can be prompted to input whether each or either of the diluting or mixing processes are needed. If each of these processes is not needed, i.e., the drug need not be diluted or mixed, complete information about, e.g., the drug's pedigree can be looked-up on e.g., the databases 62 and/or 220 (Step 655). In some examples, the information can include, e.g., a manufacturer of the drug, information about when and how the drug was shipped or received, and information about how the drug was processed by an in house pharmacy. In some examples, the utilization of the drug can be recorded in e.g., a utilization database 235 (FIGS. 2-3) (Step 660). One or more steps of the method 600 described above can be implemented by the drug labeling system 100, 300 (FIGS. 1-3).

Drug Dilution

Sometimes drugs need to be diluted before they are administered. For example, the manufacturer supplied dosage may be too strong. In these cases the final concentration of the drug is dependent upon how much diluent is added. In many cases after the drug is identified, the rules engine 120 can apply rules that require that the drug never be diluted, so that the system 100, 300 can proceed to printing the label 136. In cases where the drug needs to be diluted, the system 100, 300 may prompt the clinician 101 to provide guidance. If the clinician 101 selects "yes" to suggest that the drug needs to be diluted, the clinician 101 can then select the desired final concentration (from e.g., user-defined rules, which can include a list of approved choices that are clinically appropriate) A prompt screen on the display can, based on the rules, remind the clinician 101 how much (and what type of) diluent can be added to the original drug. The rules can also check to see if the proposed drug concentration is too strong or too weak. In some implementations, the dilution information is also printed on the label 136. In some cases, the drugs can be in the form of powders or emulsions, and need to be reconstituted into an injectable form. In such cases, the feature of system 100, 300 for dilution described above can be used to reconstitute the drug.

FIG. 7 illustrates an exemplary flowchart of a drug dilution subroutine 700 that can be used in a drug labeling process as described herein. In the drug labeling process (e.g., process 600 of FIG. 6), the clinician 101 can be prompted to indicate whether the drug needs to be diluted. In some examples, rules can be used to verify whether dilution may be permitted. If the rules permit the dilution and/or if the clinician 101 selects "yes" (Step 710), then the clinician 101 may be prompted for dilution criteria, i.e., the clinician 101 may be prompted to enter his or her desired dilution amount (Step 720). The prompting can also include "asking" the clinician 101 to add a specific amount of diluent to produce a desired end concentration. In some examples, rules are applied again to verify whether a proposed final concentration is within the prescribed guidelines (Step 740). After the final concentration of the drug is confirmed, the subroutine 700 can terminate 750 and return control to the labeling method 600 (FIG. 6). One or more steps of the subroutine 700 described above can be implemented by the drug labeling system 100, 300 (FIGS. 1-3).

Drug Mixing

In some cases two or more drugs may need to be mixed in the same syringe. For example, neostigmine and glycopyrrolate may be combined in the same syringe. Glycopyrrolate is used in conjunction with neostigmine, a neuromuscular blocking reversal agent, to prevent neostigmine's muscarinic effects such as bradycardia.

Figure 8:
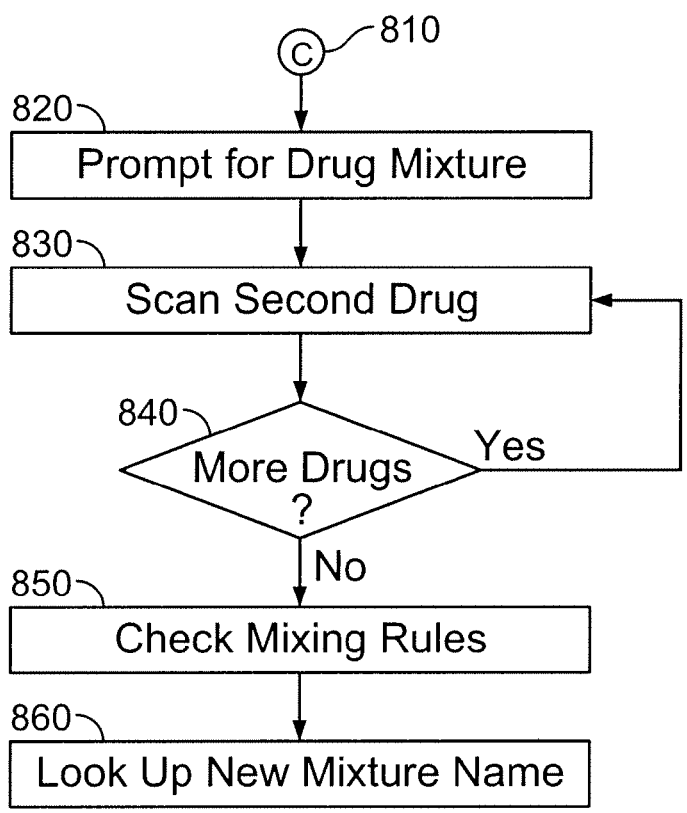
FIG. 8 is a flowchart showing a drug mixing subroutine.

FIG. 8 shows a flowchart of an exemplary drug mixing subroutine 800 that can be used in a drug labeling process as described herein. If the clinician 101 selects "yes" in the drug labeling method 600 to indicate that drug mixing is desired, subroutine 800 is called (Step 810). The clinician 101 is prompted for the drug mixture (Step 820). After the first drug is scanned, the clinician 101 can select a "mix drugs" button on the screen. The clinician 101 can then be prompted to scan in a second drug (Step 830) and, after that drug is identified, will be asked if there are more drugs to be mixed (Step 840). If there are more drugs to be mixed, the process above is repeated. If there are no additional drugs to be mixed, the mixing rules are verified (Step 850). If a violation of the rules is detected, an alert can be immediately generated and display to the clinician 101. In some implementations, the drug mixture may now have a new name. One or more databases can be consulted to provide the name for printing on the label 136 (Step 860). In some examples, the subroutine 800 can then terminate and return control to the labeling method 600 (FIG. 6). One or more steps of the subroutine 800 described above can be implemented by the drug labeling system 100, 300 (FIGS. 1-3).

In an example scenario, the drugs glycopyrrolate and neostigmine may be mixed, but only in certain ratios. Therefore, glycopyrrolate would be scanned first, then the "mix button" can be pushed. Then, neostigmine may be scanned. The rules would be applied to ensure that the drugs are mixed in an acceptable ratio before and the final mixture information is presented on the label.

Drug Administration

As described above, in some implementations, the system 100, 300 allows drug utilization to be recorded. While the pharmacy knows what drugs are purchased, it is sometimes not well understood what drugs are actually used and in what clinical context. It is generally assumed that if prepackaged drugs (drugs that are manufactured and used as a single, sterile package) need to be restocked, they were used. However, when drugs are transferred from one container to another, this may not be the case. For example, a vial may contain 50 mL of a drug but the clinician only draws up 10 mL—in this case only 20% of the drug is used. Since the labeling system 100, 300 has information regarding the drug and its final concentration, the system 100, 300 has substantially all of the information regarding the actual utilization of drugs. With respect to the tracking and reconciliation of drugs, e.g., controlled substances, the system 100, 300 can provide information about a drug's transfer, including, documentation of the chain of custody, administration, disposition, and reconciliation of controlled substances such as the opioid narcotic drugs which are essential to anesthetic care.

In some implementations, the rules engine 120 (FIG. 1) can allow for data from the identifier 128 on the first drug container 132 to be included in the information in the label 136. One advantage of this feature is that when the label 136 is later scanned by a system, e.g., a documentation system (such as AIMS), the original information on the identifier 128 can also be entered into the documentation system. In some examples, the data may be presented either in its native format or after being manipulated by the rules engine 120 to ensure compliance with the particular documentation system.

As described above, referring again to FIGS. 2 and 3, the system 100, 300 can record the drug name, pedigree, and final concentration in a database 235. In one scenario of drug utilization, use and waste of narcotics or other controlled substances can be tracked based on reports generated from the information in the database 235. For example, an initial amount of the drugs can be documented, and any unused portion of the drug (e.g., waste portion) can also be recorded. An advantage of this feature is that abuse of the drugs by e.g., clinicians 101 can be avoided.

Example System

Figure 9A:
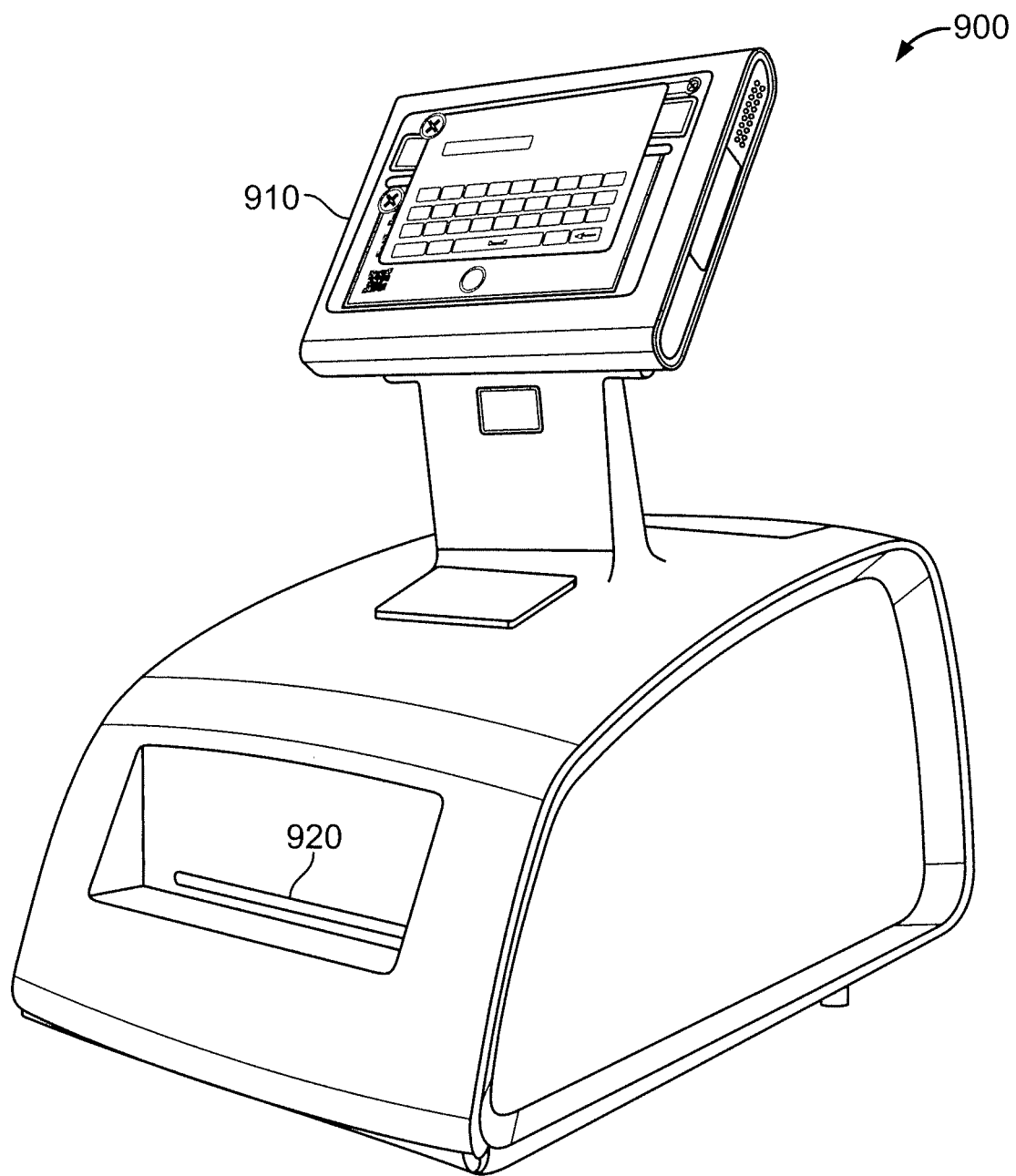
FIG. 9A is a representation of a drug labeling system.

FIG. 9A illustrates an exemplary system 900 having one or more of the features of the labeling system 100, 300 described above. The system 900 includes a user interface 910, e.g., a touch screen, for allowing a clinician 101 to provide input to the system 900 and also view information about, e.g., drugs and the transfer of the drugs. The system 900 also includes an output 920 for ejecting prepared data carriers, e.g., labels 136.

At start-up, the system 900 can perform a startup initialization and self check. The time to system 900 availability from power-on can be, e.g., less than 2 minutes. Upon startup, the system 900 can alert the clinician 101 to one or more inconvenient, unsafe or potential system operation issues. The system 900 can also prompt the clinician 101 to correct any of one or more serviceable conditions, including, conditions concerning the system 900 being off-line, out of paper, and/or out of ink. In one implementation, the system 900 can verify whether the conditions have been corrected prior to entering an operational state. The system 900 can also check for required devices such as, whether the display having the user interface 910 is connected to the system 900 and/or the existence of one or more required databases or configuration data. In one implementation, the initialization process described above can be made available to the clinician 101 from a menu, e.g., an administrative menu.

The system 900 can perform one or more test prints as a part of the initialization process to verify operation of the data carrier generator 124, e.g., the printer. The test prints can verify whether, for example, the color accuracy and/or the text or barcode printing on the label 136 is of acceptable quality. In some examples, while certain elements of accurate label printing, e.g., color and text, can be determined through the use of software components, human verification may be required to avoid compromised label quality due to other issues, including, nozzle clogs, media upside-down, and/or incorrect media. Upon the first login after start-up, the system 900 can print a test label to verify all colors can be accurately reproduced. The verification check may culminate in the presentation of a verification message to the clinician 101 requiring that the clinician 101 affirmatively acknowledge the message before the system 900 can be used to print labels 136. The acknowledgement can be logged and recorded in log files, e.g., local system log files. In some examples, on subsequent logins, if the test print operation had not been performed within the last 24 hours, the operation can be performed again. In one implementation, labels 136 may not be printed if a test print acknowledgement has not been performed in over 24 hours.

In one implementation, user identification in the form of a user login can be required to use the system 900. To facilitate easier login, the system 900 can be configured to recognize a user badge having markings, e.g., machine-readable markings, which identify the clinician 101. In some examples, the system 900 can include a "Make User Badge" function to allow for the production of user badges for identifying clinicians 101. The user badges can be encoded to be automatically recognized by the system 900 as badges assigned to clinician 101. In some examples, the user badges can include certain information, e.g., the name of the clinician 101, three letter initials for the clinician 101, an employee number for the clinician 101 and date/time the user badge was created. The "Make User Badge" function can be logged in an application log. The logged information can include, for example, the identity of the user making the badges as well as the information about the badges that were created.

Figure 9B:
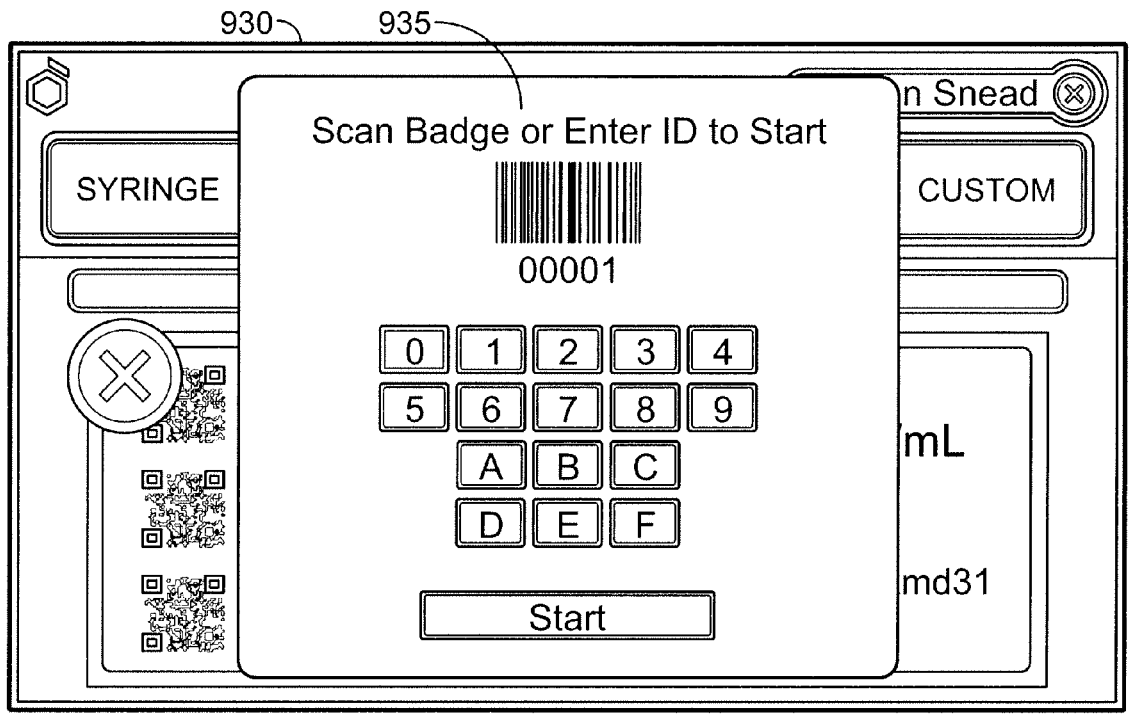
FIGS. 9B-G are representations of screenshots from a drug labeling system.
Figure 9C:
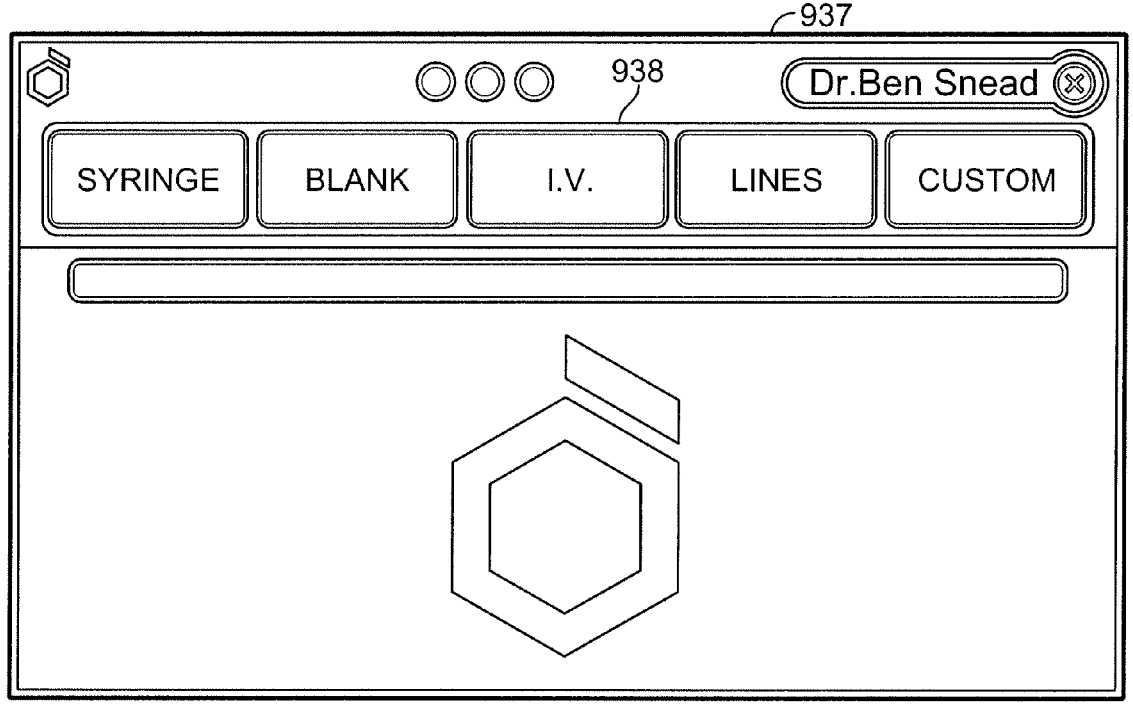

FIGS. 9B-C show example screenshots 930-980 from the user interface 910. FIG. 9B illustrates an example of a screenshot 930 that shows a prompt 935 for requesting that a clinician 101 identify himself or herself to the system 900. The clinician 101 can either scan his or her badge or enter an identification number to initialize the system 900. Once the clinician 101 has identified himself or herself to the system 900, the system 900 is ready for use. The initials of the clinician 101 creating syringe or other medical labels 136 can be logged and printed on the labels 136 for proper accountability. The system 900 can also allow user identification by methods such as, reading an RFID tag, swiping a magnetic stripe (magstripe), a user identification card and/or manual login using the touch screen interface on the system 900. In one implementation, once a valid user login barcode is scanned, the login screen can display the clinician's 101 user name as "logged in" and enabled to produce the labels 136 for the syringes. In certain implementations, some or all user login activity, including failed attempts and login method (scan or manual entry) can be logged to an audit log.

In some examples, audit logging includes logging of one or more of user, function, device specific identification information in addition to date/time of the logged actions. System logging can include similar information as well as one or more of error codes, module/class/function line number, limited tracing and/or messages produced by external interfaces.

Once logged in, the system 900 can allow for the clinician 101 to log off at any time. Additionally, the system 900 can include a configurable setting that can automatically log clinicians 101 off after a predetermined inactive time (e.g., one hour). In some examples, automatic logouts can be preceded by a warning or indication of sufficient time to allow the clinician 101 to continue by e.g., resetting the logout timeout. In some examples, the system 900 can permit one clinician 101 to exit the system 900, and allow one or more other clinicians 101 to use the system 900. Automatic logout can help insure that the clinician 900 is the true operator of the system (as recorded on labels 136 and in the audits logs). The process of logging off the system 900 can return the system 900 to the original login screen (e.g., screenshot 930).

FIG. 9C shows a screenshot 937 of an exemplary menu 938 for presenting one or more options to the clinician 101. In general, the operation of the menu 938 can be designed to be intuitive and easy even for novice and first time users. In one implementation, once logged in, the system 900 can be in, e.g., drug vial scanning mode, and can present the menu 938 on the touch screen display, including options such as, "Syringe," "Blank," "I.V.," "Lines," and "Custom" corresponding to the type of labels 136 and/or operations the clinician 101 wishes to perform. The clinician 101 can select the "Syringe" option to begin the process of scanning drug containers 132 to prepare labels 136 for syringes. In some implementations, a default option can be automatically initiated upon merely scanning the drug containers 132 without actual selection of the corresponding option. For example, once on the screen 937, the clinician 101 can simply begin scanning the drug containers 132 to produce labels 136 for syringes without needing to select the "Syringe" option. In this manner, a streamlined workflow can be implemented for producing syringe labels 136 in which much of the time is spent merely scanning drug containers 132 without any additional steps. Upon scanning, the drug container 132's barcode can be decoded and parsed to obtain the drug's NDC. As described above, the NDC can be used to lookup drug information required by the system 900. In one implementation, one or more meaningful sounds and displays can be provided to ensure that the workflow is proceeding correctly and safely. For example, if the drug's NDC is not found, the system 900 can emits a sound having a predetermined characteristic (e.g., a high frequency sound).

In one implementation, an option "Blank" can be presented to clinicians 101 for selecting preconfigured labels using graphic label representations of the drug labels 136. This option can be provided for some labeling applications that do not conform to standard drug container 132 scanning, or when the barcode on the drug container 132 is unreadable.

In certain implementations, an option "IV Label" can be presented to clinicians 101 for producing an identical pair of predetermined labels for intravenous applications having date, time and expiration information.

In one implementation, an option "Lines" can be presented to clinicians 101 for providing access to a menu (not shown) for selecting a type of "line" that is being prepared for a patient. Each option in the menu can produce a predefined label for a corresponding line. For example, an option on the menu can produce labels to identify each one of several identical-looking lines representing fluid-filled tubings that conduct body cavity or fluid pressure measurements from, e.g., an invasive catheter in a patient, to a physiological monitoring system transducer (e.g., "Arterial Line", "Pulmonary Artery Line", "Central Venous Pressure Line")

It is understood that the system described herein can be modified or extended, through, e.g., an appropriate user interface, to provide predetermined labels for other purposes, such as pathology tissue specimens or fluid samples (i.e., blood or other bodily fluids) that may be created in a medical setting, and need to be transported to a different location for analysis, together with proper identifying information about the patient, the preparer, and the identify of the specimen or fluid.

In some examples, the system 900 can provide a "Lockout" feature (not shown) that allows certain personnel, e.g., system administrators, to lock the system 900 from both authorized and unauthorized use. For example, the label printer may need servicing or have a data-set/configuration issue and consequently the system 900 may need to be locked out. An administrative function can lock the system 900 and provide for a message to be displayed on the user interface 910 while the system 900 is locked out. A configurable administrative password to unlock can be provided.

System 900 can provide internationalization of literals, local time, date and number conventions and representations. Literals can be stored in resource files that are employed based on a clinician 101's language preference. System 900 can allow configuring a system default for presenting the log in screen, but the log in screen can also provide e.g., an icon, to change the language preference. If a language preference is not set for a clinician 101, a system default will be used. If a system default is not set explicitly, US English can be set to be the default language. Resource files can be end-user accessible and provide for an override of literals protected during application updates. Resource names can be in the English language. If a resource is not set, the name of the resource preceded by an "@" symbol and all underscores converted to spaces can be displayed on the user interface 910. Common resources can be grouped to a single resource for use on different screens.

Figure 9D:
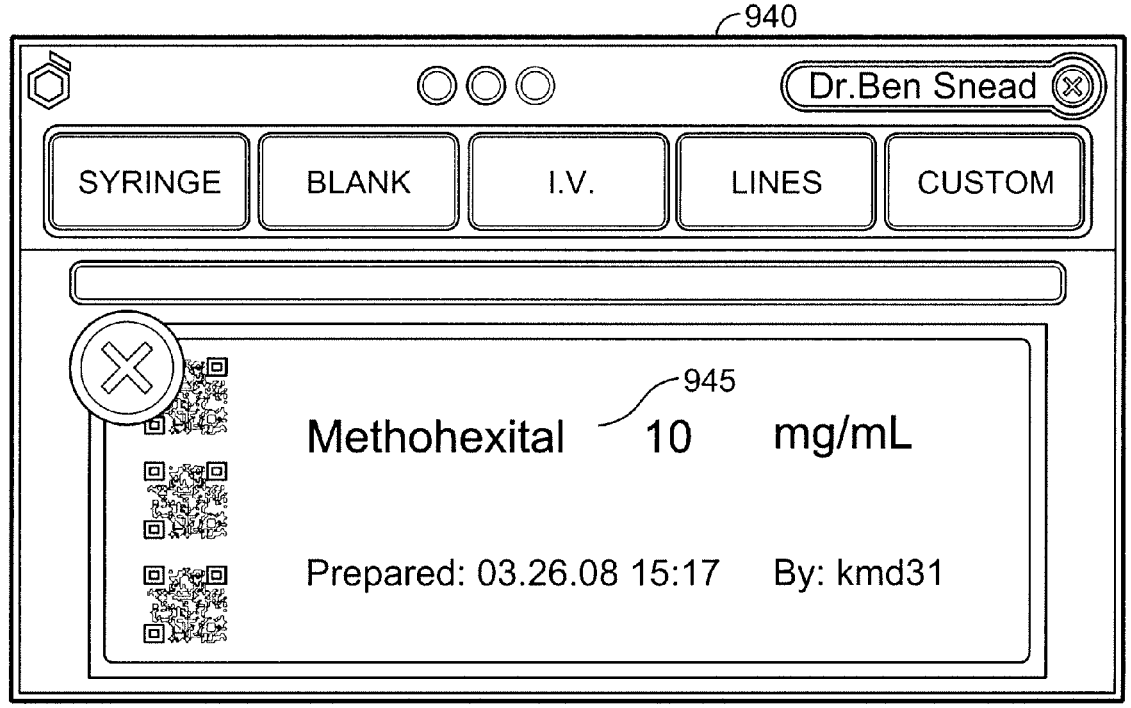

FIG. 9D shows a screenshot 940 of exemplary information that is displayed to the clinician 101. Accordingly, on scanning a drug container 132 or an identifier 128 on the drug container 132, the user interface 910 displays drug identifying data 945, e.g., the name and concentration of the drug, to the clinician 101.

Figure 9E:
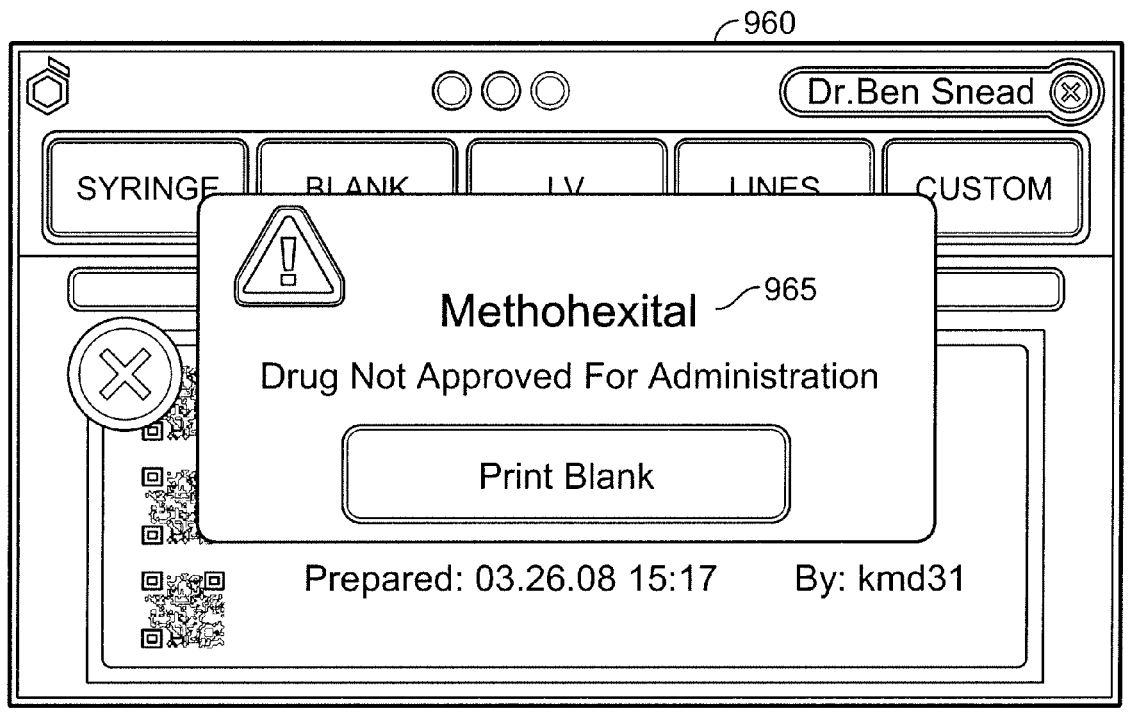

FIG. 9E shows a screenshot 960 for displaying an warning message to the clinician 101. For example, if the rules engine 120 requires that a drug, e.g., menthohexital, not be administered to a patient, the user interface 910 can display a warning message 965.

Figure 9F:
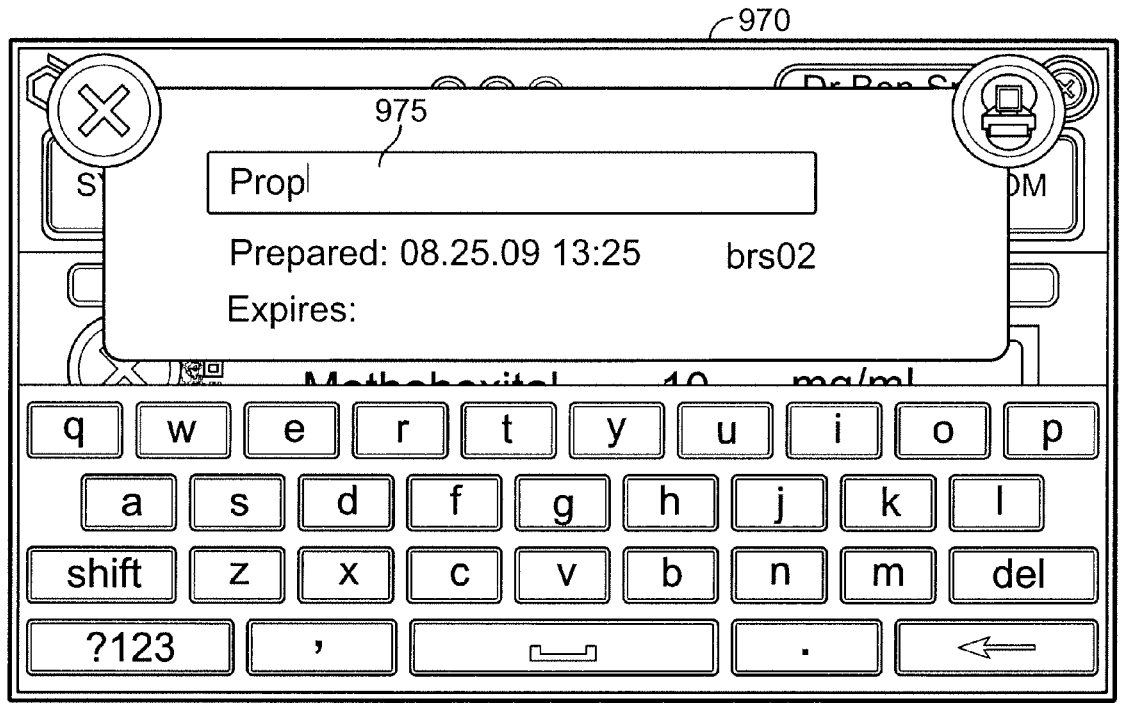
Figure 9G:
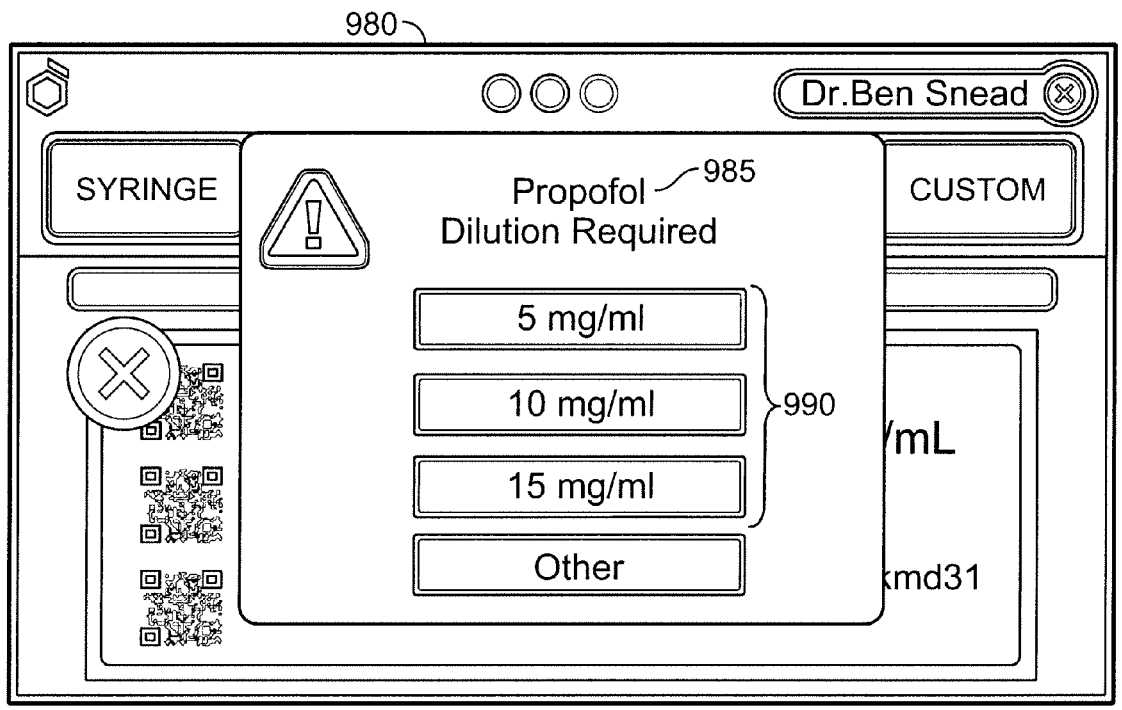

FIGS. 9F-G show screenshots 970-980 for facilitating an example drug dilution process. In screenshot 970, the clinician 101 can enter, in the text window 975, the name of a drug, e.g., propofol, to mix with menthohexital. In screenshot 980, the user interface 910 displays a prompt 985 indicating that the drug propofol needs to be diluted. Further, in some examples, the user interface 010 can also provide the clinician 101 with one or more dilution concentration options 990.

Implementation

The techniques and components of the labeling systems, processes, and computer program products described above can be implemented in digital electronic circuitry, or in computer hardware, firmware, software, or in combinations thereof. The techniques can be implemented as a computer program product, i.e., a computer program tangibly embodied in a data carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps of the techniques described herein can be performed by one or more programmable processors or computers executing a computer program to perform functions described herein by operating on input data and generating output. Method steps can also be performed by, and apparatus of the invention can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Machine-readable storage devices suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry. The computing system can include clients and servers. A client and server are generally remote from each other and typically interact over a communication network. The relationship of client and server arises by virtue of computer programs running on the respective computers and having a client-server relationship to each other.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system for enabling transfer of a drug from a first drug container to a second drug container at a specific institution, comprising:
    a drug identification component that retrieves drug identifying data for a drug in the first drug container by scanning machine-readable data on the first drug container, wherein the drug is included in a set of drugs;
    a storage medium that stores a site-specific database comprising attributes and associated values for the set of drugs including the drug in the first drug container, wherein the attributes comprise patient-independent drug policies and patient-independent drug handling guidance specific for the institution;
    a processor that obtains the drug identifying data and the attributes and associated values for the drug and produces information about the drug using the drug identifying data and the attributes and associated values;
    a rules engine that applies one or more rules to the information about the drug to generate patient-independent drug handling information; and
    an output unit that generates a label comprising the drug handling information in human-readable or machine-readable form, or both, to be affixed on the second container.

2. The system of claim 1, wherein the drug identifying data is based on a National Drug Code (NDC) number.

3. The system of claim 1, wherein the drug identifying data is based on one or more proprietary codes.

4. The system of claim 1, wherein the drug identifying data is derived from a barcode affixed to or on the first drug container.

5. The system of claim 1, wherein the drug identifying data is derived from an image of the first drug container.

6. The system of claim 1, wherein the drug identifying data is derived from a radio frequency identification (RFID) tag associated with the first drug container.

7. The system of claim 1, wherein the processor communicates with a memory and the storage medium storing the site-specific database, wherein one or both of the memory and the storage medium are local to the system.

8. The system of claim 1, wherein the processor communicates with a memory and the storage medium storing the site-specific database, wherein one or both of the memory and the storage medium are located remote from the system.

9. The system of claim 1, wherein the label is affixed on a syringe.

10. The system of claim 1, wherein the label is affixed on a vial.

11. The system of claim 1, wherein the label is affixed on an intravenous administration container.

12. The system of claim 1, wherein the label comprises information for controlling an intravenous pump or other drug delivery device.

13. The system of claim 1, wherein the rules comprise one or more of mixing rules, diluting rules, and reconstituting rules.

14. The system of claim 1, wherein the rules comprise rules for intercepting recalled, expired, or prohibited drugs.

15. The system of claim 1, wherein the rules comprise rules for drug interactions.

16. The system of claim 1, wherein the rules comprise rules for drug allergies.

17. The system of claim 1, wherein the label comprises information about pedigree of the drug.

18. The system of claim 1, wherein the label comprises one or more of a warning that the drug contains a paralyzing agent, a warning that the drug contains latex, a warning that the drug should be protected from light, and a warning that the drug should be administered directly into a muscle.

19. The system of claim 1, wherein the label comprises information enabling documentation of drug administration.

20. The system of claim 1, further comprising an audio-visual unit for producing one or more of an audible and visual indication of information about the drug.

21. The system of claim 1, wherein the label comprises information enabling a safety system to, based on the information, provide feedback to a clinician regarding one or more of a drug name, an allergic reaction to the drug, a drug amount, and an expiration date.

22. The system of claim 1, wherein the label comprises information enabling a documentation system to, based on the information, document administration of the drug.

23. The system of claim 1, further comprising a user interface to receive instructions from an authorized individual for updating the site-specific database.

24. The system of claim 23, wherein the user interface is configured to receive dose information associated with drugs in the site-specific database.

25. The system of claim 23, wherein the instructions include updates to one or more of the patient-independent drug policies and patient-independent drug handling guidance.

26. A system to record a utilization of a drug transferred from a first drug container to a second drug container at a specific institution, comprising:
a drug identification component that scans machine-readable data on a first drug container to retrieve drug identifying data for the drug, wherein the drug is included in a set of drugs;
a storage medium that stores a site-specific database comprising attributes and associated values for the set of drugs including the drug in the first drug container, wherein the attributes comprise patient-independent drug policies and patient-independent drug handling guidance specific for the institution; and
a processor configured to obtain the drug identifying data, the attributes, and the associated values for the drug, and record information regarding transfer of the drug and administration of the drug into an information management system using the drug identifying data, the attributes, and the associated values.

27. The system of claim 26, wherein the information management system is an anesthesia information management system.

28. The system of claim 26, wherein one or more of the information regarding the transfer of the drug and the information regarding administration of the drug includes a name of the drug.

29. The system of claim 26, wherein one or more of the information regarding the transfer of the drug and the information regarding administration of the drug includes a concentration of the drug.

30. The system of claim 26, wherein one or more of the information regarding the transfer of the drug and the information regarding administration of the drug includes NDC number of the drug.

31. The system of claim 26, wherein one or more of the information regarding the transfer of the drug and the information regarding administration of the drug includes drug lot number of the drug.

32. The system of claim 26, wherein one or more of the information regarding the transfer of the drug and the information regarding administration of the drug includes identity of an entity that transferred the drug.

33. The system of claim 26, wherein information regarding drug utilization documentation is used to track one or more of the utilization and waste of the drug by clinicians.

34. A method for enabling transfer of a drug from a first drug container to a second drug container at a specific institution, the method comprising:
retrieving drug identifying data for a drug in the first drug container by scanning machine-readable data on the first drug container;
retrieving from a storage medium that stores a site-specific database one or more attributes and associated values for the identified drug, wherein the attributes comprise patient-independent drug policies and patient-independent drug handling guidance specific for the institution;
based on the drug identifying data and the attributes and associated values for the drug, producing, by a processor, information about the drug;
applying, by a processor, one or more rules to the information about the drug to generate patient independent drug handling information; and
generating a label comprising the drug handling information in human-readable or machine-readable form, or both, to be affixed on the second container.

35. A computer program product stored on a computer readable storage device for enabling transfer of a drug from a first drug container to a second drug container at a specific institution, the computer program product comprising instructions to cause a computer to:
retrieve drug identifying data for a drug in the first drug container by scanning machine-readable data on the first drug container;
retrieve from a storage medium that stores a site-specific database one or more attributes and associated values for the drug, wherein the attributes comprise patient-independent drug policies and patient-independent drug handling guidance specific for the institution;
obtain the drug identifying data and the attributes and associated values for the drug and produce information about the drug using the drug identifying data and the attributes and associated values;
apply one or more rules to the information about the drug to generate patient-independent drug handling information; and
generate a label comprising the drug handling information in human-readable or machine-readable form, or both, to be affixed on the second container.

36. The system of claim 26, further comprising a user interface to receive instructions from an authorized individual for updating the site-specific database.

37. The system of claim 36, wherein the user interface is configured to receive dose information associated with drugs in the site-specific database.

38. The system of claim 36, wherein the instructions include updates to one or more of the patient-independent drug policies and patient independent drug handling guidance.

* * * * *